(12) United States Patent
Beiriger et al.

(10) Patent No.: US 9,919,091 B2
(45) Date of Patent: Mar. 20, 2018

(54) DIALYSIS SYSTEMS, COMPONENTS, AND METHODS

(71) Applicant: Fresenius Medical Care Holdings, Inc., Waltham, MA (US)

(72) Inventors: Michael James Beiriger, Pittsburgh, PA (US); Robert Dale Parks, Pittsburgh, PA (US); Ryan Christopher Kaintz, Allison Park, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 15/248,688

(22) Filed: Aug. 26, 2016

(65) Prior Publication Data

US 2016/0361483 A1    Dec. 15, 2016

Related U.S. Application Data

(62) Division of application No. 13/387,800, filed as application No. PCT/US2010/043867 on Jul. 30, 2010, now Pat. No. 9,526,820.

(60) Provisional application No. 61/231,220, filed on Aug. 4, 2009.

(51) Int. Cl.
*A61M 1/16* (2006.01)
*A61M 1/14* (2006.01)
*A61M 1/28* (2006.01)

(52) U.S. Cl.
CPC .......... *A61M 1/1694* (2013.01); *A61M 1/16* (2013.01); *A61M 1/1629* (2014.02); *A61M 1/1696* (2013.01); *A61M 1/28* (2013.01); *A61M 2205/12* (2013.01); *A61M 2205/3393* (2013.01); *A61M 2205/50* (2013.01)

(58) Field of Classification Search
CPC .. A61M 2205/12; A61M 1/1696; A61M 1/28; A61M 1/1629; A61M 1/1694; A61M 1/3413; A61M 1/342; A61M 1/3431; A61M 1/3465; A61M 2205/3393; A61M 2205/7518
USPC ......... 210/143, 175, 232, 321.6, 257.1, 646; 604/28, 29
See application file for complete search history.

(56) References Cited

U.S. PATENT DOCUMENTS

| | | |
|---|---|---|
| 3,871,913 A | 3/1975 | Shaldon |
| 4,174,231 A | 11/1979 | Hobgood |
| 4,191,351 A | 3/1980 | Goyne |

(Continued)

FOREIGN PATENT DOCUMENTS

| | | |
|---|---|---|
| CN | 1190598 A | 8/1998 |
| EP | 0 278 100 | 8/1988 |

(Continued)

OTHER PUBLICATIONS

"RX Guide to Custom Dialysis," COBE Renal Care Inc., Revision E. Sep. 1993.

(Continued)

*Primary Examiner* — Dirk Bass
(74) *Attorney, Agent, or Firm* — Fish & Richardson P.C.

(57) ABSTRACT

A dialysis system including a housing, a dialysate pump disposed in the housing, and a dialysate line configured to be operatively connected to the dialysate pump such that the dialysate pump can pump dialysate through the dialysate line when the dialysate line is in fluid communication with a dialysate source.

9 Claims, 22 Drawing Sheets

(56) References Cited

U.S. PATENT DOCUMENTS

| | | | |
|---|---|---|---|
| 4,581,141 A | 4/1986 | Ash | |
| 4,661,246 A * | 4/1987 | Ash | A61M 1/1696 210/110 |
| 4,666,598 A | 5/1987 | Heath et al. | |
| 4,684,460 A | 8/1987 | Issautier | |
| 4,728,496 A | 3/1988 | Petersen et al. | |
| 4,770,787 A | 9/1988 | Heath et al. | |
| 4,784,495 A | 11/1988 | Jonsson et al. | |
| 4,789,467 A | 12/1988 | Lindsay et al. | |
| 4,997,577 A | 3/1991 | Stewart | |
| 5,213,483 A | 5/1993 | Flaherty et al. | |
| 5,256,371 A | 10/1993 | Pippert | |
| 5,262,068 A | 11/1993 | Bowers et al. | |
| 5,277,820 A | 1/1994 | Ash | |
| 5,304,349 A | 4/1994 | Polaschegg | |
| 5,409,612 A | 4/1995 | Maltais et al. | |
| 5,421,813 A | 6/1995 | Ohnishi | |
| 5,536,412 A | 7/1996 | Ash | |
| 5,589,070 A | 12/1996 | Maltais et al. | |
| 5,591,344 A | 1/1997 | Kenley et al. | |
| 5,603,902 A | 2/1997 | Maltais et al. | |
| 5,605,630 A | 2/1997 | Shibata | |
| 5,713,125 A | 2/1998 | Watanabe et al. | |
| 5,788,099 A | 8/1998 | Treu et al. | |
| 5,919,369 A | 7/1999 | Ash | |
| 5,944,684 A | 8/1999 | Roberts et al. | |
| 6,000,567 A | 12/1999 | Carlsson et al. | |
| 6,036,858 A | 3/2000 | Carlsson et al. | |
| 6,086,753 A | 7/2000 | Ericson et al. | |
| 6,143,181 A | 11/2000 | Falkvall et al. | |
| 6,170,785 B1 | 1/2001 | Lampropoulos et al. | |
| 6,190,855 B1 | 2/2001 | Herman et al. | |
| 6,277,277 B1 | 8/2001 | Jacobi et al. | |
| 6,280,632 B1 | 8/2001 | Polaschegg | |
| 6,308,721 B1 | 10/2001 | Bock | |
| 6,409,699 B1 | 6/2002 | Ash | |
| 6,416,293 B1 | 7/2002 | Bouchard et al. | |
| 6,428,706 B1 | 8/2002 | Rosenqvist et al. | |
| 6,484,383 B1 | 11/2002 | Herklotz | |
| 6,672,841 B1 | 1/2004 | Herklotz et al. | |
| 6,743,201 B1 | 6/2004 | Doenig et al. | |
| 6,755,976 B2 | 6/2004 | Rosenqvist et al. | |
| 6,878,283 B2 | 4/2005 | Thompson | |
| 7,033,498 B2 | 4/2006 | Wong | |
| 7,077,956 B2 | 7/2006 | Rovatti | |
| 7,241,272 B2 | 7/2007 | Karoor et al. | |
| 7,789,849 B2 | 9/2010 | Busby et al. | |
| 7,947,179 B2 | 5/2011 | Rosenbaum et al. | |
| 8,192,387 B2 | 6/2012 | Brugger et al. | |
| 8,235,931 B2 | 8/2012 | Burbank et al. | |
| 2002/0079695 A1 | 6/2002 | Campbell et al. | |
| 2003/0105424 A1 | 6/2003 | Karoor et al. | |
| 2004/0019312 A1 | 1/2004 | Childers et al. | |
| 2004/0050789 A1 | 3/2004 | Ash | |
| 2005/0274658 A1 | 12/2005 | Rosenbaum et al. | |
| 2007/0158247 A1 | 7/2007 | Carr et al. | |
| 2007/0158249 A1 | 7/2007 | Ash | |
| 2007/0158268 A1 | 7/2007 | DeComo | |
| 2007/0161113 A1 | 7/2007 | Ash | |
| 2007/0161941 A1 | 7/2007 | Ash et al. | |
| 2007/0181499 A1 | 8/2007 | Roberts et al. | |
| 2007/0185430 A1 | 8/2007 | Brugger et al. | |
| 2008/0149563 A1 | 6/2008 | Ash | |
| 2008/0177216 A1 | 7/2008 | Ash | |
| 2008/0200869 A1 | 8/2008 | Bedingfield | |
| 2009/0005686 A1 | 1/2009 | Yanagihara et al. | |
| 2009/0008306 A1 | 1/2009 | Cicchello et al. | |
| 2009/0107902 A1 | 4/2009 | Childers et al. | |
| 2009/0114595 A1 | 5/2009 | Wallenas et al. | |
| 2009/0127193 A1 | 5/2009 | Updyke et al. | |
| 2010/0317782 A1 | 12/2010 | Hattori et al. | |
| 2011/0303588 A1 | 12/2011 | Kelly et al. | |
| 2011/0315611 A1 | 12/2011 | Fulkerson et al. | |

FOREIGN PATENT DOCUMENTS

| | | |
|---|---|---|
| EP | 0 673 658 | 9/1995 |
| EP | 0 947 814 | 10/1999 |
| EP | 1 195 171 | 10/2002 |
| EP | 1 342 480 | 10/2003 |
| EP | 1 096 991 | 6/2004 |
| JP | 11347115 | 12/1999 |
| JP | 2003-000704 | 1/2003 |
| JP | 2004209103 | 7/2004 |
| JP | 2008178444 | 8/2008 |
| WO | WO9702055 | 1/1997 |
| WO | WO9702056 | 1/1997 |
| WO | WO9817333 | 4/1998 |
| WO | WO9937342 | 7/1999 |
| WO | WO0230267 | 4/2002 |
| WO | WO0243859 | 6/2002 |
| WO | WO2005123230 | 12/2005 |
| WO | WO2006036876 | 4/2006 |
| WO | WO2006088419 | 8/2006 |
| WO | WO2007028056 | 3/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |

OTHER PUBLICATIONS

"Sorbent Dialysis Pimer," COBE Renal Care, Inc., Sep. 4, 1993 Ed.
Blumenkrantz et al., "Artif Organs," 3(3):230-236, 1978.
Operator's Manual—Fresenius 2008K Hemodialysis Machine (2000).
International Search Report and Written Opinion, PCT/US2010/043867, dated Dec. 17, 2010; pp. 1-16.
Sleep Safe Operating Instructions, Part 677 805 1, Fresenius Medical Care, 1st edition, Aug. 2000, 133 pages.
Sleep Safe Technical Manual, Part 677 8011, Fresenius Medical Care, 1st edition, Aug. 2000, 174 pages.

* cited by examiner

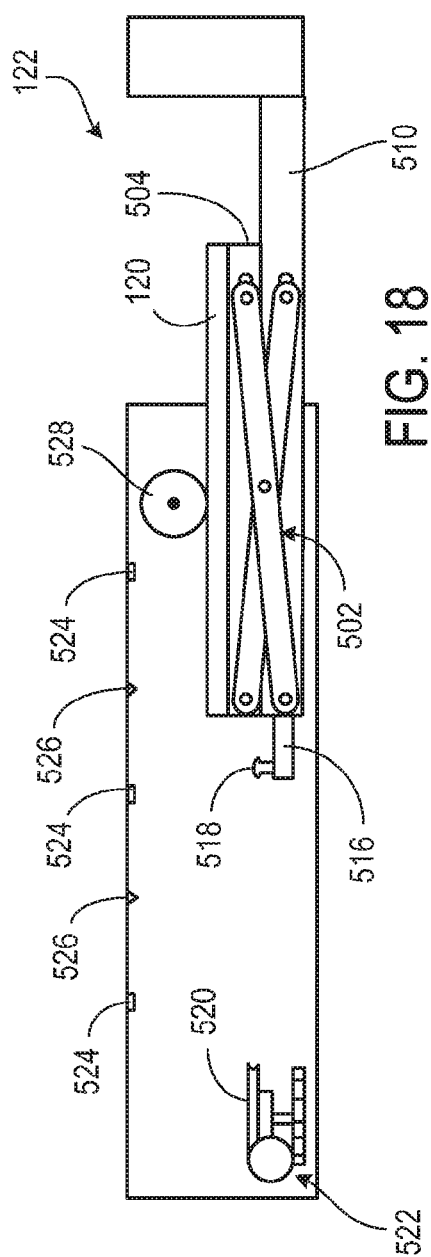
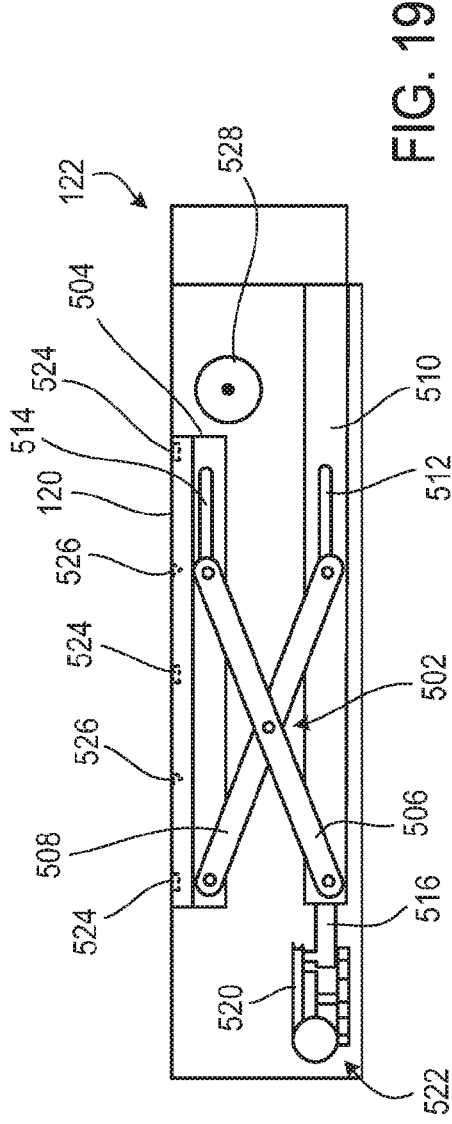

DIALYSIS SYSTEMS, COMPONENTS, AND METHODS

CROSS-REFERENCE TO RELATED APPLICATIONS

This application is a divisional of and claims priority under 35 U.S.C. § 120 to U.S. Ser. No. 13/387,800, filed May 14, 2012, which is a 371 of International Application No PCT/US2010/043867, filed Jul. 30, 2010, which claims the benefit of U.S. Application Ser. No. 61/231,220, filed on Aug. 4, 2009. The entire contents of these priority applications are incorporated herein by reference.

TECHNICAL FIELD

This disclosure relates to dialysis systems, components, and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with sterile aqueous solution, referred to as PD solution or dialysate. The membranous lining of the patient's peritoneum acts as a natural semi-permeable membrane that allows diffusion and osmosis exchanges to take place between the solution and the blood stream. These exchanges across the patient's peritoneum result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a dialysis system includes a housing and a dialysate pump disposed in the housing. The dialysate pump is positioned above a cavity defined by the housing. The system also includes a slidable drawer at least partially disposed within the cavity of the housing. The drawer is connected to the housing in a manner such that when the drawer is moved to a closed position within the cavity, a member of the drawer is lifted towards the dialysate pump positioned above the cavity. The system further includes a dialysate line connected to the member of the drawer and configured to be operatively connected to the dialysate pump when the drawer is moved to the closed position and the member of the drawer is lifted such that the dialysate pump can pump dialysate through the dialysate line when the dialysate line is in fluid communication with a dialysate source.

In another aspect of the invention, a dialysis system includes a sorbent device, a dialysate reservoir fluidly connected to the sorbent device and arranged to collect dialysate exiting the sorbent device, a first pump in fluid communication with the sorbent device, and a second pump in fluid communication with the dialysate reservoir. The first pump is positioned upstream of the sorbent device and is configured to introduce dialysate into the sorbent device. The second pump is positioned downstream of the sorbent device and is configured to draw dialysate out of the dialysate reservoir.

In an additional aspect of the invention, a hemodialysis system includes a first module including a blood pump, a blood line operatively connected to the blood pump such that the blood pump can pump blood through the blood line when the blood line is in fluid communication with a blood source, a dialyzer fluidly connected to the blood line, a second module that is separate from the first module and includes a dialysate pump, and a dialysate line operatively connected to the dialysate pump such that the dialysate pump can pump dialysate through the dialysate line when the dialysate line is in fluid communication with a dialysate source. The dialysate line is fluidly connected to the dialyzer.

Implementations can include one or more of the following features.

In certain implementations, the dialysate line is secured to a dialysate component carrier that is connected to the member of the drawer.

In some implementations, the dialysate component carrier snaps into the drawer.

In certain implementations, the dialysate line extends across an aperture formed by the dialysate component carrier.

In some implementations, the aperture is configured to receive a pump of the second module therein.

In certain implementations, the dialysate component carrier defines an aperture overlying the dialysate line.

In some implementations, the dialysis system further includes a heater arranged to be aligned with the aperture such that heat emitted from the heater warms dialysate passing through the dialysate line.

In certain implementations, the drawer includes a mechanical lifting mechanism operatively secured to the member of the drawer.

In some implementations, the dialysis system further includes a blood line operatively connected to a blood pump such that the blood pump can pump blood through the blood line.

In certain implementations, the system further includes a dialyzer to which the dialysate line and the blood line are fluidly connected.

In some implementations, the dialysis system is a hemodialysis system.

In certain implementations, the sorbent device is absorbent.

In some implementations, the dialysate reservoir is vented to atmosphere.

In certain implementations, the second pump is adapted to draw fluid from the dialysate reservoir at substantially the same rate that the first pump introduces dialysate into the sorbent device.

In some implementations, the dialysis system further includes a connector line that fluidly connects the sorbent device to the dialysate reservoir.

In certain implementations, one end of the connector line is connected to a top region of the sorbent device, and another end of the connector line is connected to a top region of the dialysate reservoir.

In some implementations, the sorbent device and the dialysate reservoir sit on a weight scale.

In certain implementations, the dialysis system further includes a microprocessor connected to the scale and the first and second pumps.

In some implementations, the microprocessor is adapted to control the first and second pumps in a manner to maintain a substantially constant weight on the scale.

In certain implementations, the first and second modules are releasably secured to one another.

In some implementations, the first module is positioned on top of the second module.

In certain implementations, the first module comprises at least one weight scale.

In some implementations, the at least one weight scale is configured to be stored in a cavity formed in the first module.

In certain implementations, the at least one weight scale is pivotably connected to the side of the first module.

In some implementations, the dialysis system further includes a dialysate component carrier to which the dialysate line is secured.

In certain implementations, the dialysate line extends across an aperture formed by the dialysate component carrier.

In some implementations, the aperture is configured to receive a pump of the second module therein.

Implementations can include one or more of the following advantages.

In some implementations, the dialysate component carrier is positioned below the pumps and valves of the dialysis machine. As a result, in the event of a leak in any of the components secured to the dialysate component carrier, the dialysate is prevented from contacting the pumps and valves of the dialysis machine. Similarly, in certain implementations, the dialysate component carrier is contained within a compartment (e.g., a drawer) of the dialysis machine such that, in the event of a leak, the dialysate can be contained within the compartment.

In certain implementations, a drawer in which the dialysate component carrier is disposed is configured to automatically lift the dialysate component carrier as the drawer is closed. As a result, the components secured to the dialysate component carrier can be engaged with corresponding instruments (e.g., pumps, sensors, etc.) of the dialysis machine in a single step taken by the user (i.e., by shutting the drawer).

In some implementations, the system includes a dialysate reservoir that is positioned downstream of the sorbent device and in fluid communication with the sorbent device. The dialysate reservoir contains a sufficient volume of dialysate to meet the demands of the dialysis machine. For example, in some cases, the sorbent device absorbs some of the dialysate that is introduced into the sorbent device via a dialysate inlet line. As a result, the amount of dialysate exiting the sorbent device is less than the amount of dialysate entering the sorbent device. By drawing dialysate into a dialysate outlet line from the dialysate reservoir rather than directly from the sorbent device, a substantially constant volumetric flow rate can be achieved in the dialysate inlet and outlet lines. Similarly, if the dialysate absorbed by the sorbent device is released and introduced back into the dialysate circuit such that the amount of dialysate exiting the sorbent device exceeds the demand of the dialysis machine, the excess dialysate can be retained within the dialysate reservoir. By removing that excess dialysate from the circuit and storing it in the dialysate reservoir, a substantially constant volumetric flow rate can be maintained in the dialysate inlet and outlet lines.

Other aspects, features, and advantages will be apparent from the description and drawings, and from the claims.

DESCRIPTION OF DRAWINGS

FIG. 18 is a side schematic view of the bottom module of the portable hemodialysis system of FIG. 1, with the drawer of the module fully open such that a scissor mechanism of the drawer is in a lowered position.

FIG. 19 is a side schematic view of the bottom module of the portable hemodialysis system of FIG. 1, with the drawer of the module fully closed such that the scissor mechanism of the drawer is in a raised position.

DETAILED DESCRIPTION

Figure 1:
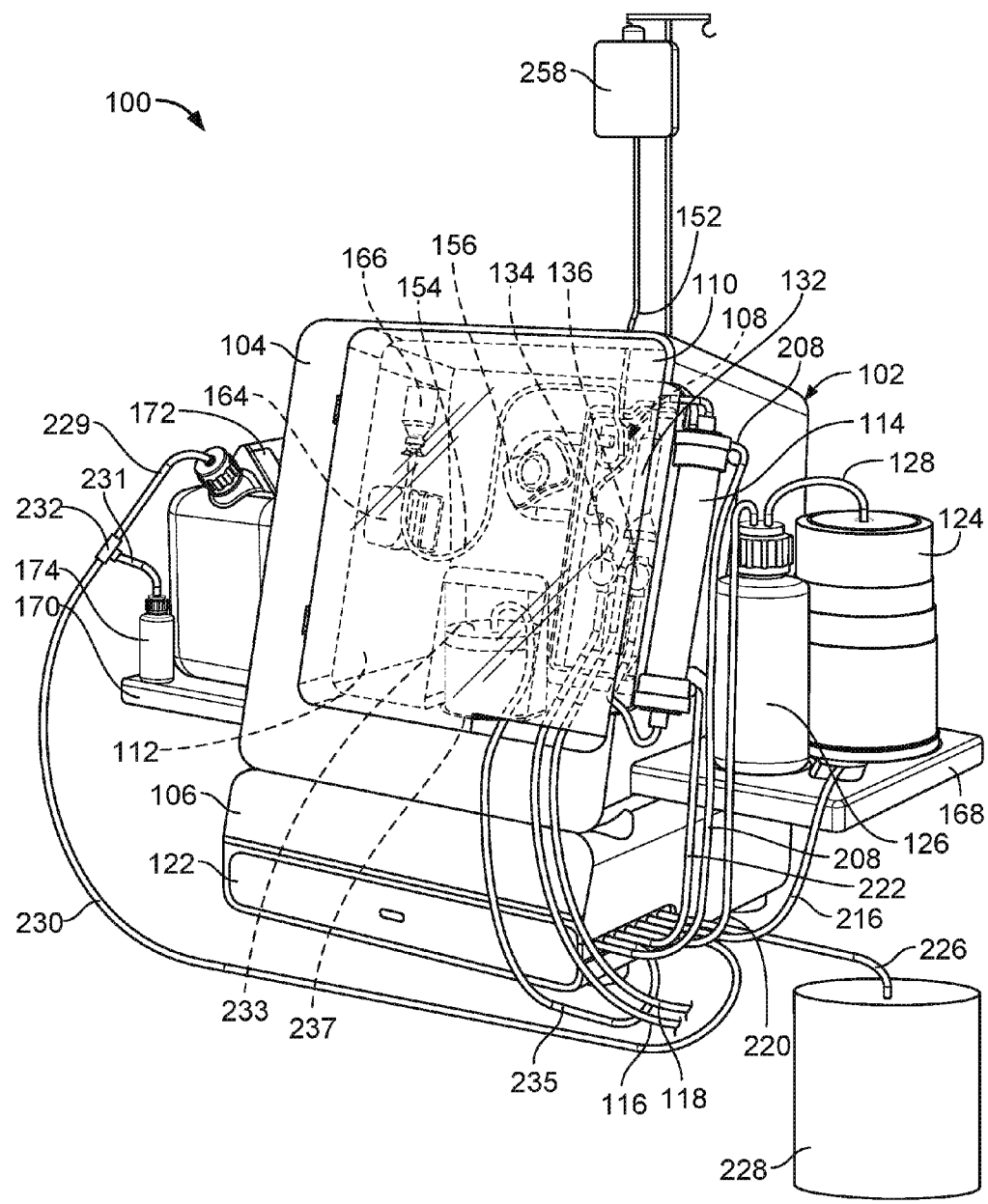
FIG. 1 is a perspective view of a portable hemodialysis system.

Referring to FIG. 1, a portable hemodialysis system 100 includes a hemodialysis machine 102 having a top module 104 that rests on a bottom module 106. A blood component carrier 108 is secured between a door 110 and a front face 112 of the top module 104. Various blood lines and other blood components, including a dialyzer 114, are secured to the blood component carrier 108. During use, arterial and venous patient lines 116, 118 are connected to a patient to allow blood to flow through a blood circuit formed by the various blood lines, the dialyzer 114, and various other components connected to the blood component carrier 108. A dialysate component carrier 120 (shown in FIG. 2) is contained within a drawer 122 of the bottom module 106. Various dialysate lines and other dialysate components are connected to the dialysate component carrier 120. The dialysate lines are connected to, among other components, the dialyzer 114, a sorbent device 124, and a dialysate reservoir 126. The sorbent device 124 and the dialysate reservoir 126 are connected to one another by a connector line 128. During use, dialysate is circulated through a dialysate circuit formed by the dialysate lines, the dialyzer 114, the sorbent device 124, the dialysate reservoir 126, and various other components of the dialysate component carrier 120. As a result, the dialysate passes through the dialyzer 114 along with the blood. The blood and dialysate passing through the dialyzer 114 are separated from one another by a permeable structure (e.g., a permeable membrane and/or permeable microtubes). As a result of this arrangement, toxins are removed from the blood and collected in the dialysate as the blood and dialysate pass through the dialyzer 114. The filtered blood exiting the dialyzer 114 is returned to the patient. The dialysate that exits the dialyzer 114 includes toxins removed from the blood and is commonly referred to as "spent dialysate." The spent dialysate is routed from the dialyzer 114 to the sorbent device 124 where the toxins, including urea, are stripped from the spent dialysate. The resulting liquid exiting the sorbent device 124 (referred to herein as "recycled dialysate") is then circulated back through the dialysate circuit and re-used to filter blood of the patient.

Figure 2:
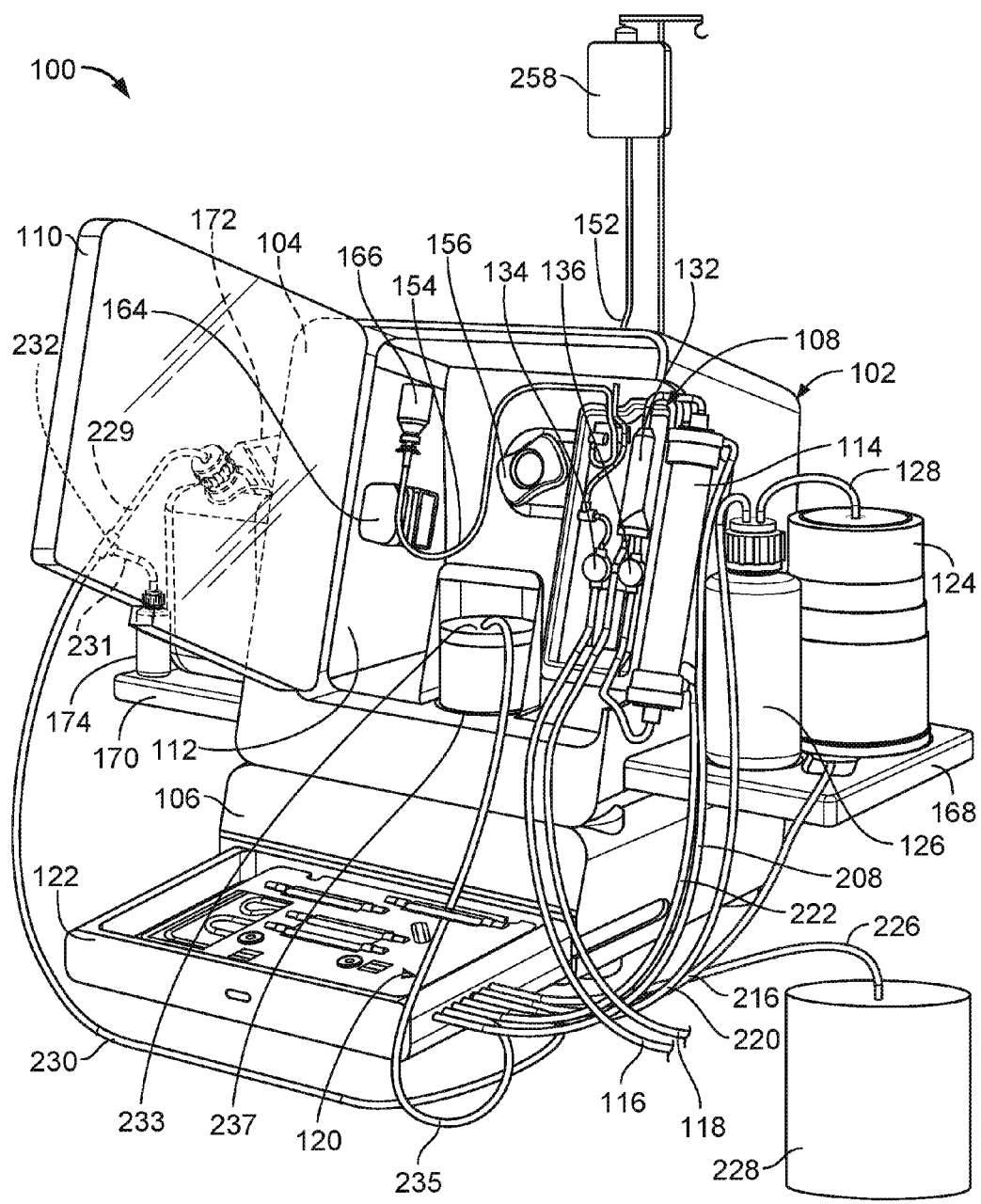
FIG. 2 is a perspective view of the portable hemodialysis system of FIG. 1 with a door open to expose a blood component carrier and with a drawer open to expose a dialysate component carrier.

FIG. 2 illustrates the hemodialysis system 100 with the door 110 of the top module 104 and the drawer 122 of the bottom module 106 open to expose the blood component carrier 108 and the dialysate component carrier 120. The blood component carrier 108 can be secured to the front face 112 of the top module 104 using any of various attachment techniques. In some implementations, the blood component carrier 108 is secured to the front face 112 of the top module 104 by inserting projections extending from a rear surface of a body 130 of the blood component carrier 108 into mating recesses formed in the top module 104 of the hemodialysis machine 102. The blood component carrier 108 can alternatively or additionally be secured to the front face 112 of the top module 104 using other types of mechanical connectors (e.g., clips, clamps, screws, etc.). In addition, the door 110 includes an inflatable pad that is inflated after closing the door 110 to compress the blood component carrier 108 and its components between the door 110 and the front face 112 of the top module 104. The dialysate component carrier 120 sits within a recess formed by the drawer 122. As discussed below, when the drawer 122 is closed, the dialysate component carrier 120 and its components are mechanically lifted to compress the dialysate component carrier 120 and its components against an instrument bearing horizontal surface of the top module 104. As discussed in greater detail below, by compressing the blood component carrier 108 and the dialysate component carrier 120 against surfaces of the top and bottom modules 104 and 106, respectively, certain components secured to the carriers 108, 120 are brought into operative engagement with associated devices (e.g., pumps, sensors, etc.) on the surfaces of the modules 104, 106.

Figure 3:
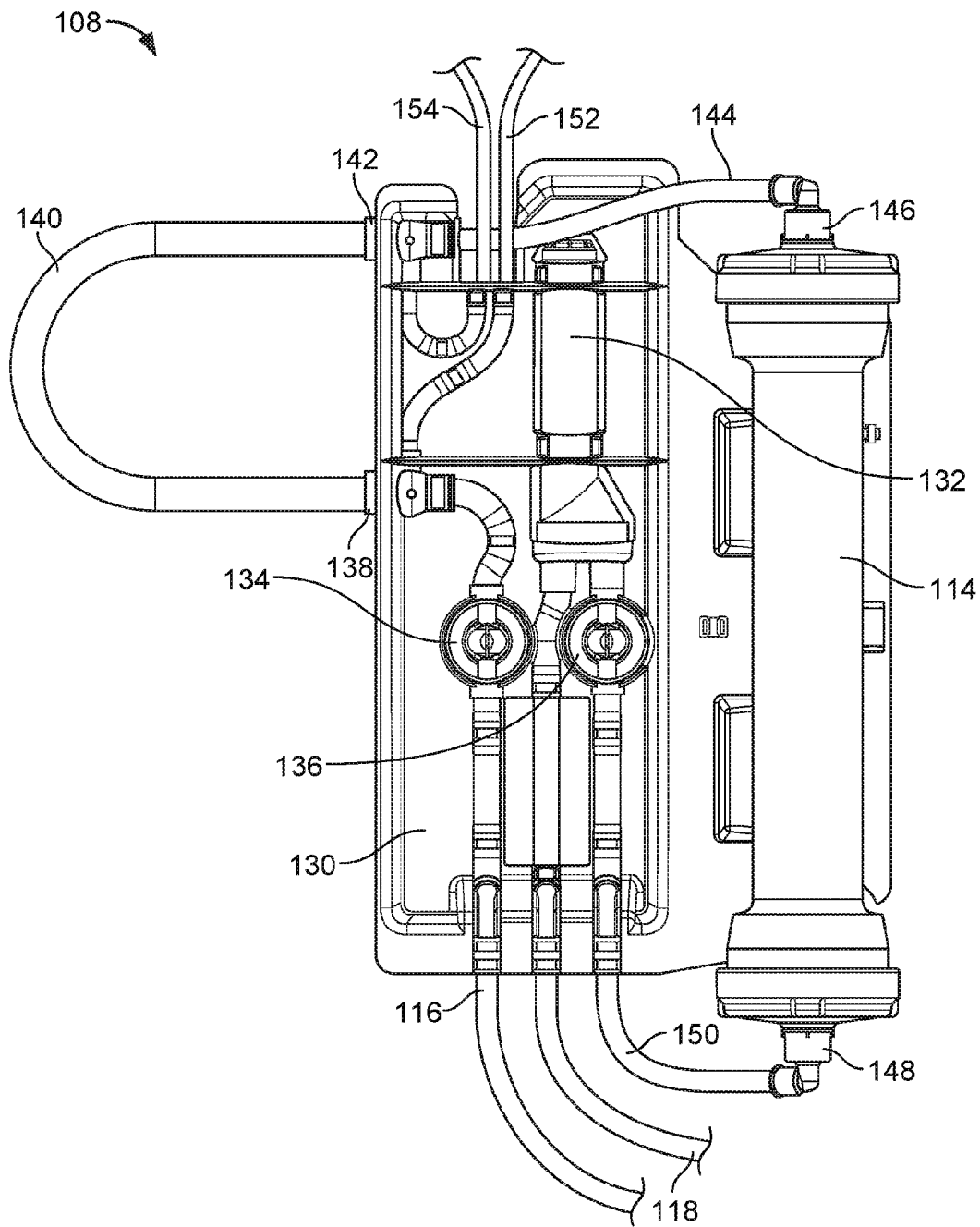
FIG. 3 is a front view of the blood component carrier of the portable hemodialysis system of FIG. 1.
Figure 4:
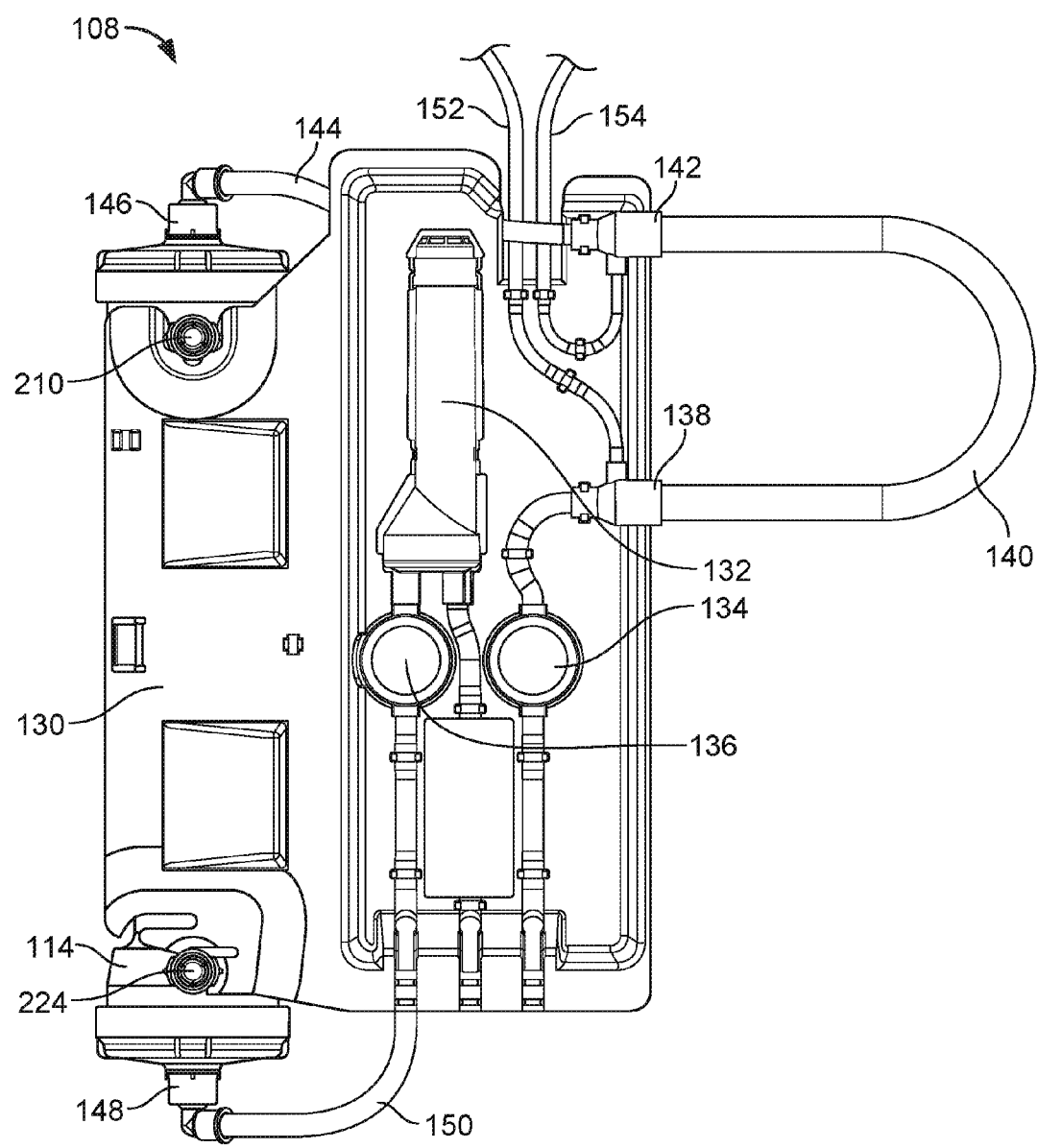
FIG. 4 is a back view of the blood component carrier of the portable hemodialysis system of FIG. 1.

As shown in FIGS. 3 and 4, the blood component carrier 108 holds various different blood components. The molded body 130 of the blood component carrier 108 forms a series of apertures and recesses for capturing and retaining the various blood lines and components. The body 130 includes a recessed portion (shown on the left side of FIG. 3 and the right side of FIG. 4) and a flat portion (shown on the right side of FIG. 3 and the left side of FIG. 4). The recessed portion is configured to retain most of the blood components while the flat portion is configured to hold the dialyzer 114.

Still referring to FIGS. 3 and 4, an air release chamber 132 is snapped into an aperture formed in the body 130 of the carrier 108. In some implementations, projections from the body 130 extend part way around the air release chamber 132 to retain the air release chamber 132 securely in the carrier. The air release chamber 132 allows gas, such as air, to escape from blood in the blood circuit and out of the chamber through a vent positioned at the top of the chamber. Examples of suitable air release chambers are described in U.S. Patent Application Publication No. 2007/0106198 and U.S. Patent Application Publication No. 2009-0071911, which are incorporated by reference herein.

Pressure sensor capsules 134, 136 are similarly positioned in apertures formed in the body 130 of the carrier 108. A suitable capsule can include a thin membrane on one side (i.e., on the side that faces the front face 112 of the top module 104 during use) through which pressure in the capsule can be determined by a pressure sensor (e.g., a pressure transducer) on the front face 112 of the top module 104 during use. The carrier 108 can be arranged so that the thin membrane is placed in close proximity to or in contact with the pressure sensor on the front face 112 of the top module 104 during use. Suitable capsules are described further in U.S. Pat. No. 5,614,677, "Diaphragm gage for measuring the pressure of a fluid," which is incorporated herein by reference.

The arterial patient line 116 is contained within a recess formed in the body 130 of the blood component carrier 108. One end of the arterial patient line 116 is fluidly connected to an artery of a patient during treatment. The arterial patient line 116 is also fluidly connected to the capsule 134. The capsule 134 allows pressure in the arterial patient line 116 to be sensed by a mating pressure sensor on the front face 112 of the top module 104 of the hemodialysis machine 102 during treatment. The arterial patient line 116 extends along the recess to a first pump line adaptor 138, which connects the arterial patient line 116 to one end of a U-shaped pump line 140. The other end of the pump line 140 is connected to a second pump line adaptor 142, which is in fluid connection with a dialyzer inlet line 144. The dialyzer inlet line 144 is connected via a tube adaptor to a blood entry port 146 of the dialyzer 114. A blood exit port 148 of the dialyzer 114 is connected to another tube adaptor, which connects the dialyzer 114 to a dialyzer outlet line 150. The capsule 136 is positioned along the dialyzer outlet line 150, upstream of the air release chamber 132. The air release chamber 132 includes both an entry port and an exit port along its bottom surface. The capsule 136 is fluidly connected to the entry port. The venous patient line 118 extends from the air release chamber 132 and is fluidly connected to a vein of a patient during treatment.

Still referring to FIGS. 3 and 4, in addition to the blood lines forming the main blood circuit described above, a priming line 152 and a drug line 154 are connected to the blood circuit for introducing priming solution, such as saline, and drugs, such as heparin, into the blood circuit. The priming line 152 is connected to the first pump line adaptor 138, and the drug line 154 is connected to the second pump line adaptor 142.

The various blood lines, priming line 152, and drug line 154 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate. In some implementations, the blood component carrier body 130 is formed of PVC, polyethylene, polypropylene, polystyrene, and/or high density polyethylene. The various blood lines, priming line 152, and drug line 154 are typically retained within recessed channels formed in the carrier body 130. The recessed channels can have a diameter equal to or slightly less than the diameters of the lines so that the lines are retained within the channels with a friction fit. Alternatively or additionally, any of various other techniques can be used to secure the lines to the carrier body 130. For example, mechanical attachment devices (e.g., clips or clamps) can be attached to the carrier body 130 and used to retain the lines. As another example, the lines can be adhered to or thermally bonded to the carrier body 130.

Suitable blood component carriers and their related components are described in greater detail in U.S. Patent Application Publication No. 2009/0101566, entitled "Dialysis Systems and Related Components," which is incorporated by reference herein.

Figure 5:
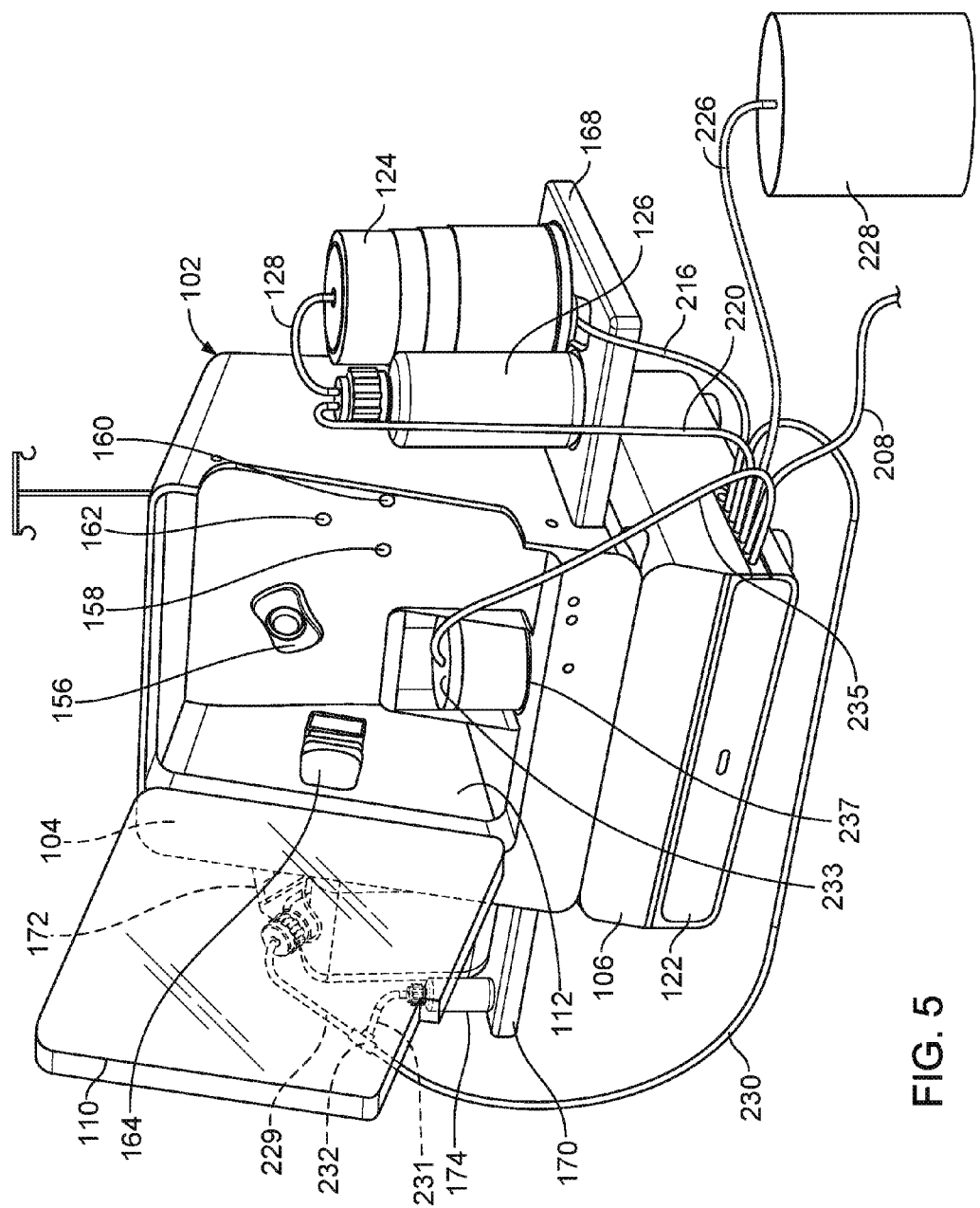
FIG. 5 is a perspective view of the portable hemodialysis system of FIG. 1 with the door open and the blood component carrier removed.

FIG. 5 is a perspective view of the hemodialysis system 100 with the blood component carrier 108 and its blood lines and components removed from the top module 104. As shown in FIG. 5, a blood pump 156 extends from the front face 112 of the top module 104. The blood pump 156 is a peristaltic pump and is arranged so that the U-shaped pump line 140 extending laterally from the blood component carrier 108 is positioned around the peristaltic pump when the blood component carrier 108 is secured to the front face 112 of the top module 104. The top module 104 also includes pressure sensors (e.g., pressure transducers) 158, 160 that align with the pressure sensor capsules 134, 136 of the blood component carrier 108 when the blood component carrier 108 is secured to the front face 112 of the top module 104. The pressure sensors 158, 160 are adapted to measure the pressure of blood flowing through the capsules 134, 136. In addition, the top module 104 includes a level detector 162 that aligns with the air release chamber 132 when the blood component carrier 108 is secured to the front face 112 of the top module 104. The level detector 162 is adapted to detect the level of blood within the air release chamber 132. The level detector 162 can, for example, include an ultrasonic transmitter/receiver for determining the level of blood in the air release chamber 132. A drug pump 164 also extends from the front face 112 of the top module 104. The drug pump 164 is a peristaltic pump with an external housing. During use, the drug line 154 extending from the blood component carrier 108 can be connected to a heparin vial 166 (shown in FIGS. 1 and 2) and operatively positioned within the housing of the drug pump 164 in a manner such that rolling members of the drug pump 164 operatively engage the drug line 154. The drug pump 164 can then be activated to inject heparin into the blood passing through the blood lines (i.e., the pump line 140) of the blood component carrier 108.

Referring again to FIG. 1, load cell scales 168, 170 extend from opposite sides of the top module 104. The sorbent device 124 and the dialysate reservoir 126 sit on the scale 168 extending from one side of the module 104, and a dilution water container 172 and a sodium chloride solution container 174 sit on the scale 170 extending from the opposite side of the top module 104. As described in greater detail below, the sorbent device 124, the dialysate reservoir 126, the dilution water container 172, and the sodium chloride solution container 174 are fluidly connected to dialysate lines and components of the dialysate component carrier 120 within the drawer 122 of the bottom module 106. During use, the contents of the sorbent device 124, the dialysate reservoir 126, the dilution water container 172, and the sodium chloride solution container 174 are delivered to and pass through the dialysate lines and various other components secured to the dialysate component carrier 120. As the volumes of liquid within the sorbent device 124, the dialysate reservoir 126, the dilution water container 172, and the sodium chloride solution container 174 change, the load applied to the load cell scales 168, 170 also changes, causing the scales 168, 170 to move slightly. The load cell scales 168, 170 include strain gauges that can detect slight movement of the scales 168, 170. A change in liquid volume can thus be determined using the strain gauge. Monitoring the volumes of liquid contained in the sorbent device 124, the dialysate reservoir 126, the dilution water container 172, and the sodium chloride solution container 174 can help to ensure that desired amounts of those liquids are delivered to the dialysate within the dialysate circuit.

Figure 6:
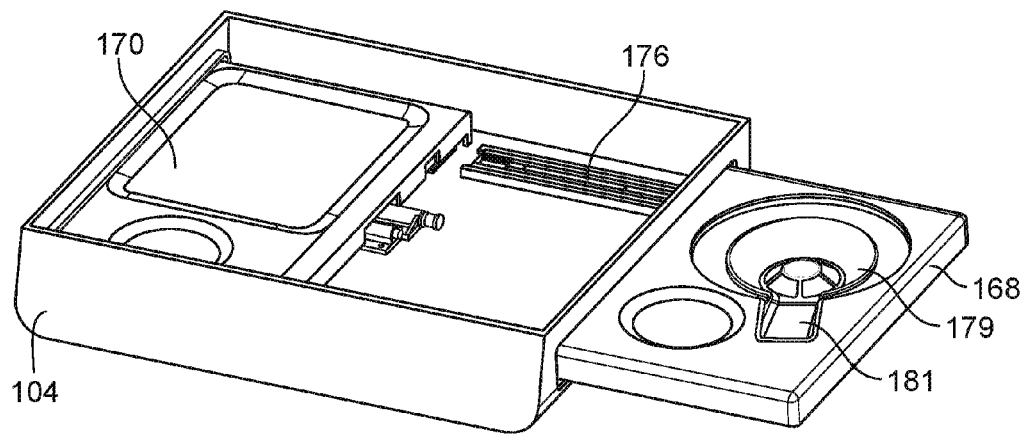
FIGS. 6 and 7 are cut-away views of a portion of the system that includes retractable scales.
Figure 7:
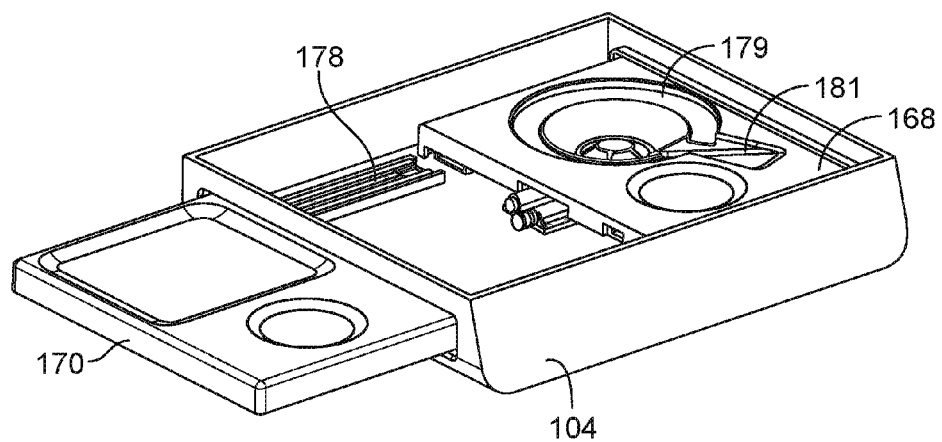

FIGS. 6 and 7 are cut-away views of the top module 104 with the sorbent device 124, the dialysate reservoir 126, the dilution water container 172, and the sodium chloride solution container 174 removed from the scales 168, 170. As shown in FIGS. 6 and 7, the scales 168, 170, when not in use, can be pushed into a cavity formed by the top module 104. The scales 168, 170 are secured to the bottom surface of the top module 104 via slidable tracks 176, 178. This arrangement permits the scales 168, 170 to be extended from the sides of the top module 104 for use and to be pushed into a cavity formed in the top module 104 for storage. By pushing the scales 168, 170 into the cavity for storage, the overall footprint of the system 100 can be reduced, making it easier to transport the system 100.

Still referring to FIGS. 6 and 7, the scales 168, 170 include recessed regions that are sized and shaped to retain the sorbent device 124, the dialysate reservoir 126, the dilution water container 172, and the sodium chloride solution container 174. A recess 179 for retaining the sorbent device 124 also includes a depression 181 in which a dialysate line extending from the dialysate component carrier 120 can be disposed to connect the fluid line to a fluid fitting at the bottom of the sorbent device 124.

Figure 8:
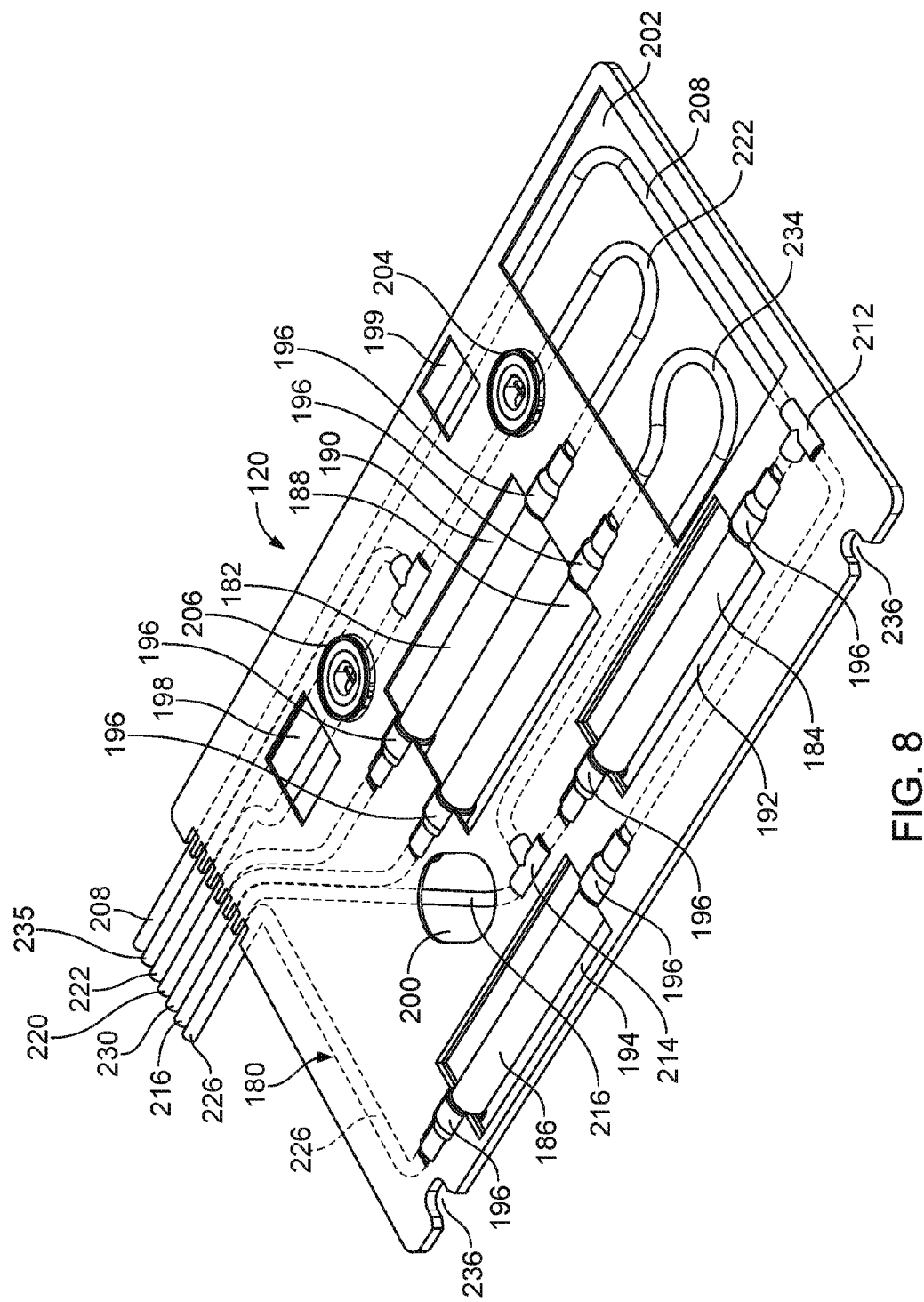
FIG. 8 is a perspective view of the dialysate component carrier of the portable hemodialysis system of FIG. 1.
Figure 9:
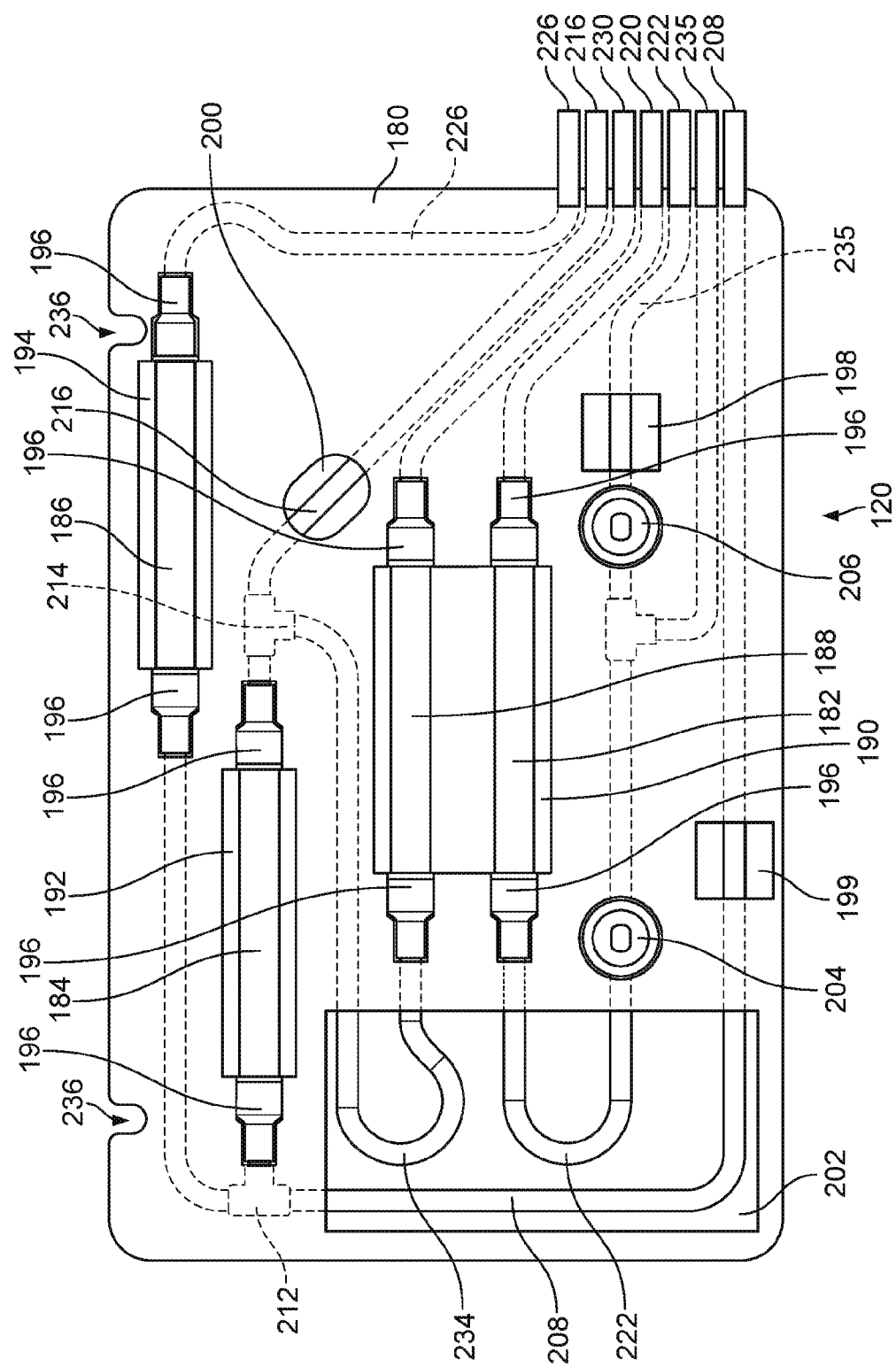
FIG. 9 is a plan view of the dialysate component carrier of the portable hemodialysis system of FIG. 1

FIG. 8 is a perspective view of the dialysate component carrier 120, and FIG. 9 is a top, plan view of the dialysate component carrier 120. As shown in FIGS. 2, 8, and 9, the dialysate component carrier 120 holds various different dialysate components. The carrier has a molded body 180, which includes apertures and recesses for capturing and retaining the various dialysate lines and components.

Five pump lines (i.e., a dialyzer inlet pump line 182, a dialyzer outlet pump line 184, an ultrafiltrate pump line 186, a dilution water/sodium chloride solution pump line 188, and an infusate pump line 189) are positioned within apertures 190, 192, 194, 195 formed in the carrier body 180. Connectors 196, which are attached to opposite ends of each of the pump lines 182, 184, 186, 188, 189, are secured to the carrier body 180. In particular, the connectors 196 are snapped into mating recesses formed in the carrier body 180. The recesses are sized to securely retain the connectors 196 when they are snapped into the recesses. Alternatively or additionally, other attachment techniques, such as clipping, clamping, adhering, and/or thermal bonding, can be used to secure the connectors 196 to the carrier body 180. The apertures 190, 192, 194, 195 across which the pump lines 182, 184, 186, 188, 189 extend are sized and shaped to receive pumps positioned in the bottom module 106 of the hemodialysis machine 102 during use, as discussed below. When those pumps are received within the apertures 190, 192, 194, 195, the pump lines 182, 184, 186, 188, 189 engage the pumps and conform to the surfaces of the pumps.

In addition to the apertures 190, 192, 194, 195, the carrier body 180 includes apertures 198, 199, 200, and 202 that are arranged to permit a conductivity meter, a blood leak detector, a temperature sensor, and a heater, respectively, in the bottom module 106 of the hemodialysis machine to access fluid lines underlying those apertures, as will be discussed in greater detail below.

A pressure sensor capsule 204 is positioned in an aperture formed in the body 180 of the carrier 120. A suitable capsule can include a thin membrane on one side through which pressure in the capsule 204 can be determined by a pressure sensor (e.g., a pressure transducer) in the bottom module 106 during use. The dialysate component carrier can, for example, be arranged so that the thin membrane is placed in close proximity to or in contact with the pressure sensor in the bottom module 106. Suitable capsules are described further in U.S. Pat. No. 5,614,677, entitled "Diaphragm gage for measuring the pressure of a fluid," which is incorporated herein by reference.

An ammonium sensor capsule 206 is also secured within an aperture formed in the carrier body 180. The ammonium sensor capsule 206 is arranged to cooperate with an ammonium sensor located in the bottom module 106.

Still referring to FIGS. 2, 8, and 9, one end of a dialyzer outlet line 208 is connected to a dialysate outlet port 210 (shown in FIG. 4) of the dialyzer 114 during use. The opposite end of the dialyzer outlet line 208 is connected to a T-connector 212. The T-connector 212 includes one port connected to a line leading to the dialyzer outlet pump line 184. The line leading to the dialyzer outlet pump line 184 is connected to the connector 196 at one end of the dialyzer outlet pump line 184. The connector 196 at the opposite end of the dialyzer outlet pump line 184 is connected to a line that leads to another T-connector 214. One of the ports of the T-connector 214 is connected to a sorbent device inlet line 216. The sorbent device inlet line 216 is fluidly connected to a fluid fitting at the bottom of the sorbent device 124 during use. As discussed above, the sorbent device 124 is fluidly connected to the dialysate reservoir 126 by the connector line 128 such that dialysate can flow from the sorbent device 124 to the dialysate reservoir 126 during treatment. One end of a dialysate reservoir outlet line 220 is in fluid communication with the dialysate reservoir 126 during use. The opposite end of the dialysate reservoir outlet line 220 is connected to one of the connectors 196 of the dialyzer inlet pump line 182, and a dialyzer inlet line 222 is connected to the connector 196 at the opposite end of the dialyzer inlet pump line 182. The dialyzer inlet line 222 is fluidly connected to the pressure sensor capsule 204 and the ammonium sensor capsule 206 and leads back to the dialyzer 114 where it is connected to a dialysate entry port 224 (shown in FIG. 4) of the dialyzer 114.

In addition to the dialysate lines described above, which form the main dialysate circuit, additional fluid lines are secured to the carrier body 180 and fluidly connected to the main dialysate circuit to permit fluids to be added and removed from the main dialysate circuit. Still referring to FIGS. 2, 8, and 9, one end of a fill/drain line 226 is connected to a fill/drain container 228. The other end of the fill/drain line 226 is connected to one of the connectors 196 of the ultrafiltrate pump line 186. The connector 196 at the opposite end of the ultrafiltrate pump line 186 is connected to a line leading back to the T-connector 212. As discussed below, the fill/drain line 226 permits dialysate to be transferred from the fill/drain container 228 during fill phases of operation and permits fluid to be removed from the main dialysate circuit and transferred to the fill/drain container 228 during drain phases of operation.

One end of a dilution water/sodium chloride outlet solution line 230 is fluidly connected via a three-way valve 232 to a dilution water outlet line 229 in the dilution water container 172 and to a sodium chloride solution outlet line 231 in the sodium chloride solution container 174 during use. The opposite end of the dilution water/sodium chloride solution outlet line 230 is connected to one of the connectors 196 of the dilution water/sodium chloride solution pump line 188. A dilution water/sodium chloride solution injection line 234 is connected to the connector 196 at the opposite end of the pump line 188. The dilution water/sodium chloride injection line 234 is connected at its opposite end to the T-connector 214 arranged along the sorbent device inlet line 216. This arrangement allows dilution water and sodium chloride solution to be injected into the dialysate flowing through the sorbent device inlet line 216 during treatment.

Still referring to FIGS. 2, 8, and 9, an infusate jar 233 is fluidly connected via an infusate injection line 235 to the dialysate circuit. One end of the infusate injection line 235 is inserted into the infusate jar 233 and the other end of the infusate injection line 235 is connected to one of the connectors 196 of the infusate pump line 189. An infusate connector line 239 is connected to the other connector 196 of the infusate pump line 189. The infusate connector line 239 is connected at its opposite end to a T-connector 241, which is positioned along the dialyzer inlet line 222. As a result of this arrangement, the infusate connector line 239 provides fluid communication between the infusate pump line 189 and the dialyzer inlet line 222.

The infusate jar 233, as shown in FIG. 2, sits on a load cell scale 237 connected to the front face 112 of the top module 104 of the hemodialysis machine 102. The load cell scale 237 is adapted to detect mass change resulting from a change of volume of infusate solution within the infusate jar 233.

As discussed above, in addition to the apertures 190, 192, 194, 195 in which the pump lines 182, 184, 186, 188, 189 are positioned, the carrier body 180 includes apertures 198, 199, 200 that overly portions of the dialyzer inlet line 222, the dialyzer outlet line 208, and the sorbent device inlet line 216, respectively. These apertures 198, 199, 200 expose the lines 222, 208, 216 from the top side of the carrier 120. As discussed below, this arrangement allows sensors positioned in the bottom module 106 of the hemodialysis machine 102 to access the lines during treatment. The large aperture 202 exposes portions of each of the dialyzer outlet line 208, the dialyzer inlet line 222, and the dilution water/sodium chloride solution injection line 234 from a top side of the carrier 120. As described below, this aperture 202 permits heat to be applied to those lines from a heater positioned in the bottom module 106 of the hemodialysis machine 102 during treatment in order to maintain the fluids passing therethrough within an acceptable temperature range.

The dialysate lines discussed above can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate. In some implementations, the dialysate carrier body 180 is formed of PVC, polyethylene, polypropylene, polystyrene, and/or high density polyethylene. The various dialysate lines and components described above can be secured to the dialysate carrier body 180 using any of the techniques discussed above for securing the blood lines and components to the blood component carrier body 130.

As shown in FIG. 2, the dialysate component carrier 120, sits within a recess of the drawer 122. The dialysate component carrier 120 is secured to the drawer 122 in a manner such that the pump lines 182, 184, 186, 188, 189 align with associated pumps in the bottom module 106 when the drawer 122 is pushed fully into the drawer cavity of the bottom module 106 and engaged. The drawer 122 includes locating pins that cooperate with slots 236 (shown in FIGS. 8 and 9) formed in the dialysate component carrier body 180 to maintain the dialysate component carrier 120 in a desired position relative to the drawer 122. In particular, the locating pins engage the back edge of the carrier body 180 that forms the slots 236 while the front edge of the carrier body 180 engages a front wall of the drawer 122. As a result, the locating pins limit the movement of the dialysate component carrier 120 within the drawer 122 and thus help to ensure that the pump lines 182, 184, 186, 188, 189, the sensor capsules 204, 206, and the apertures 198, 199, 200, 202 of the dialysate component carrier 120 align with their associated instruments in the bottom module 106 of the hemodialysis machine 102 during treatment.

Figure 10:
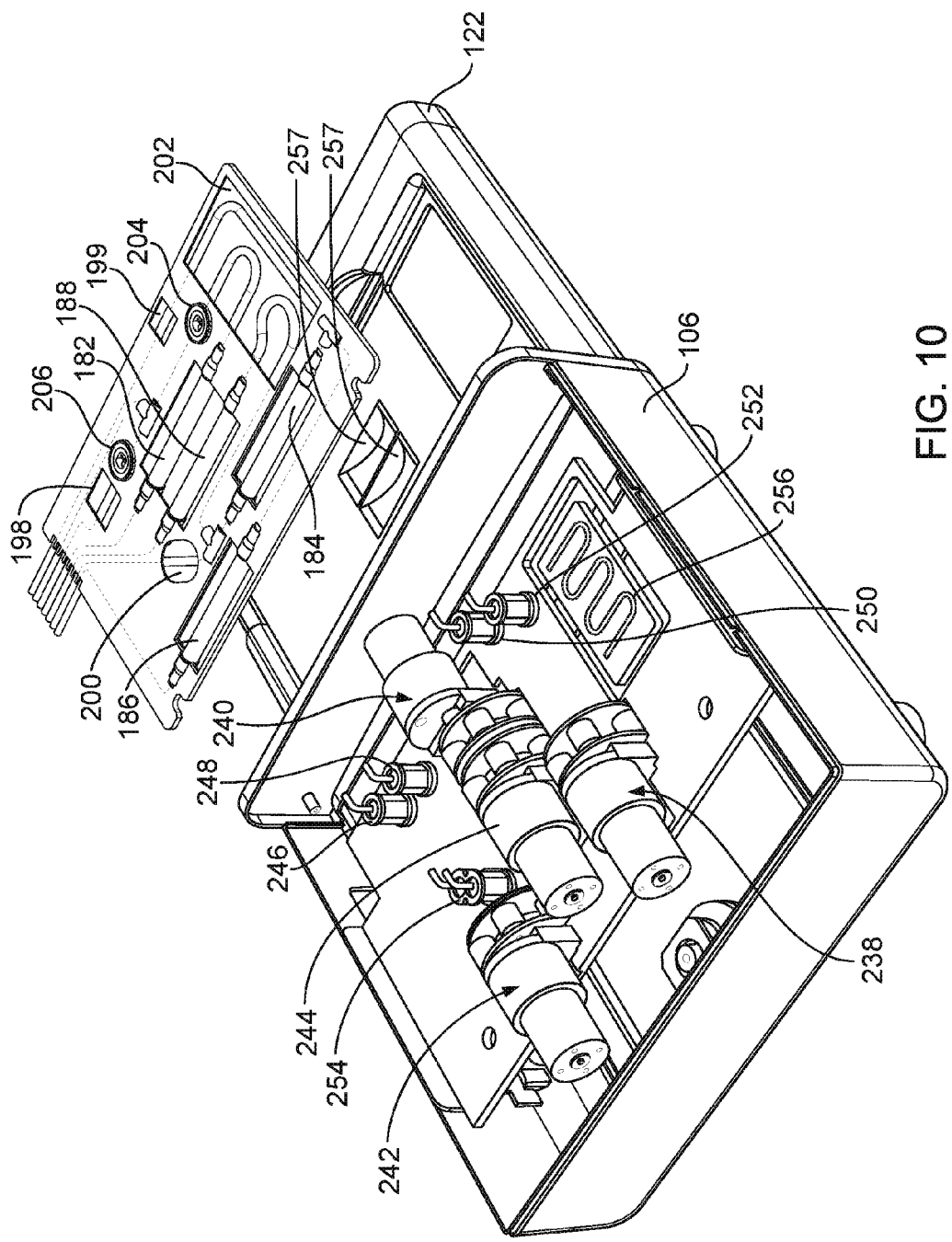
FIG. 10 is a cut-away view of a portion of the portable hemodialysis system of FIG. 1 with the drawer open and various internal components of the hemodialysis system exposed.

FIG. 10 is a cut away view of the bottom module 106, which shows a dialyzer outlet pump 238, a dialyzer inlet pump 240, an ultrafiltrate pump 242, a dilution water/sodium chloride solution pump 244, an infusate pump 245, a conductivity meter 246, an ammonium sensor 248, a blood leak detector 250, a pressure sensor 252, a temperature sensor 254, and a heater 256 positioned above the drawer cavity of the bottom module 106. Each of the pumps 238, 240, 242, 244 is a peristaltic pump that includes multiple rolling members positioned about the circumference of a rotatable frame. When the pump lines 182, 184, 186, 188, 189 are pressed against the rolling members of the pumps 238, 240, 242, 244, 245, the pump lines 182, 184, 186, 188, 189 deflect into recesses or raceways 257 formed along the bottom surface of the drawer 122. As the pump frames are rotated, the rolling members apply pressure to the associated pump lines and force fluid through the pump lines.

The conductivity meter 246, the ammonium sensor 248, the blood leak detector 250, the pressure sensor 252, and the temperature sensor 254 can be any of various devices capable of detecting the conductivity, ammonium level, blood, pressure, and temperature, respectively, of fluid passing through the lines associated with those instruments.

The heater 256 is capable of raising the temperature of the fluid flowing through the dialyzer outlet line 208, the dialyzer inlet line 222, and the dilution water/sodium chloride solution injection line 234 to a desired temperature (e.g., about body temperature) and then maintaining the flowing fluid within an acceptable temperature range. Any of various different types of heaters that are sufficiently compact to fit within the bottom module 106 of the dialysis can be used. In some implementations, the heater is a resistance heater. In certain implementations, the heater is an inductance heater. Any of various other types of heaters can alternatively or additionally be used.

The hemodialysis machine 102 also includes a microprocessor to which the pumps 238, 240, 242, 244, 245, the three-way valve 232, the weight scales 168, 170, 237, the sensors 248, 250, 252, 254, and the heater 256 are connected. These instruments can be connected to the microprocessor in any manner that permits signals to be transmitted from the instruments to the microprocessor and vice versa. In some implementations, electrical wiring is used to connect the microprocessor to the instruments. Wireless connections can alternatively or additionally be used. As described below, the microprocessor can control the pumps 238, 240, 242, 244, 245, the valve 232, and the heater 256 based on information received from the scales 168, 170, 237 and the sensors 246, 248, 250, 252, 254.

Referring to FIGS. 18 and 19, which show the drawer 122 of the bottom module 106 in a fully open and fully closed position, respectively, the drawer 122 includes a scissor mechanism 502 on which a platen 504 is situated. The dialysate component carrier 120 sits on top of the platen 504. When the drawer 122 is pushed into the cavity of the bottom module 106, the platen 504 and the dialysate component carrier 120 are automatically raised by the scissor mechanism 502 such that the dialysate components and dialysate lines of the carrier 120 engage associated instruments inside the dialysis machine. Although FIGS. 18 and 19 show only the left scissor mechanism 502 of the drawer 122, it should be understood that the drawer 122 also includes a right scissor mechanism. Because the structure and functionality of the left and right scissor mechanisms are substantially the same, only the left scissor mechanism 502 will be described in detail below.

The scissor mechanism 502 includes two elongate members 506, 508 that are pinned together in a central region of each elongate member such that the elongate members 506, 508 can rotate relative to one another. The rear end region of the elongate member 506 (i.e., the end region of the elongate member 506 on the left in FIGS. 18 and 19) is pinned to a base 510 of the drawer 122, and the rear end region of the elongate member 508 (i.e., the end region of the elongate member 508 on the left in FIGS. 18 and 19) is pinned to the platen 504 of the drawer 122 on which the dialysate component carrier 120 rests. Due to this arrangement, the rear end regions of the elongate members 506, 508 are able to pivot relative to the base 510 and the platen 504, but the rear end regions of the elongate members 506, 508 are not allowed to move translationally (i.e., in the direction of movement of the drawer as it is opened and closed) relative to the base 510 and the platen 504. The front end regions of the elongate members 506, 508 (i.e., the end regions of the elongate members 506, 508 on the right in FIGS. 18 and 19) are also pinned to the base 510 and the platen 504, respectively. The portions of the base 510 and the platen 504 to which the front end regions of the elongate members 506, 508 are pinned define slots 512, 514 (shown in FIG. 19) in which the pins are allowed to move translationally. When the front end regions of the elongate members 506, 508 are positioned at the front ends of the slots 512, 514, as shown in FIG. 18, the scissor mechanism 502 is in a lowered position. When the front end regions of the elongate members 506, 508 are positioned at the rear ends of the slots 512, 514, as shown in FIG. 19, the scissor mechanism 502 is in a raised position. Because the base 510 of the drawer 122 is not free to move in the vertical direction but the platen 504 is free to move in the vertical direction, the platen 504 is raised and lowered as the scissor mechanism 502 is raised and lowered. Thus, by controlling the translational position of the front end regions of the elongate members 506, 508, the height of the platen 504 in the dialysate component carrier 120 can be controlled.

A pull plate 516 is secured to the pin that rides within the slot 512 and secures the elongate member 508 to the base 510 of the drawer 122. The pull plate 516 is similarly secured to a pin that rides within a slot formed in the right-hand side of the base of the drawer and secures an elongate member of the right scissor mechanism to the base of the drawer. The pull plate 516 extends rearward toward the rear end of the drawer 122, and the rear end region of the pull plate 516 includes a bearing pin 518 extending therefrom. The bearing pin 518 is located at the rear of the dialysate drawer 122 and is configured to engage a cam 520 positioned near the rear of the dialysis machine when the drawer is closed. The cam 520 is secured to a cam drive (e.g. a worm drive) 522. The cam drive 522 is configured to rotate the cam 520. When the bearing pin 518 of the pull plate 516 is engaged with the cam 520 and the cam 520 is rotated by the cam drive 522, the rotation of the cam 520 moves of the pull plate 516 in a translational direction. Depending on the direction of rotation of the cam 520, the pull plate 516 can be moved in a rearward or frontward direction.

Multiple projections 524 and alignment pins 526 extend downward from the top surface of the bottom module 106 forming the drawer cavity. The projections 524 are configured to keep the dialysate component carrier 128 a desired distance away from the top surface of the bottom module 106 when the scissor mechanism 502 is raised, as shown in FIG. 19. The projections 524 can, for example, engage the top surface of the platen 504 as the platen 504 is raised by the scissor mechanism 502. Alternatively or additionally, the projections 524 can engage the dialysate component carrier itself to maintain the dialysate component carrier 120 a desired distance away from the top surface of the bottom module 106.

The alignment pins 526 are conical shaped and configured to mate with recesses formed in the top surface of the platen 504 when the platen 504 and the dialysate component carrier 120 are raised. The alignment pins 526 help to ensure that the dialysate component carrier 120 is properly aligned with respect to the top surface of the bottom module 106 so that the various dialysate components and dialysate lines of the dialysate component carrier 120 align with and engage their corresponding instruments on the top surface of the bottom module 106. As an alternative to or in addition to mating with recesses formed in the top surface of the platen 504, the alignment pins 526 can mate with recesses formed in the dialysate component carrier itself.

The bottom module 106 further includes a wheel 528 that rides along the top surface of the platen 504 as the drawer 122 is closed. By riding along the top surface of the platen 504, the wheel 528 prevents the scissor mechanism 502 from expanding prematurely. Once the drawer 122 has been closed a sufficient amount such that the front end of the platen 504 has passed the wheel 528, the wheel 528 no longer prevents the scissor mechanism 502 from expanding.

Figure 20:
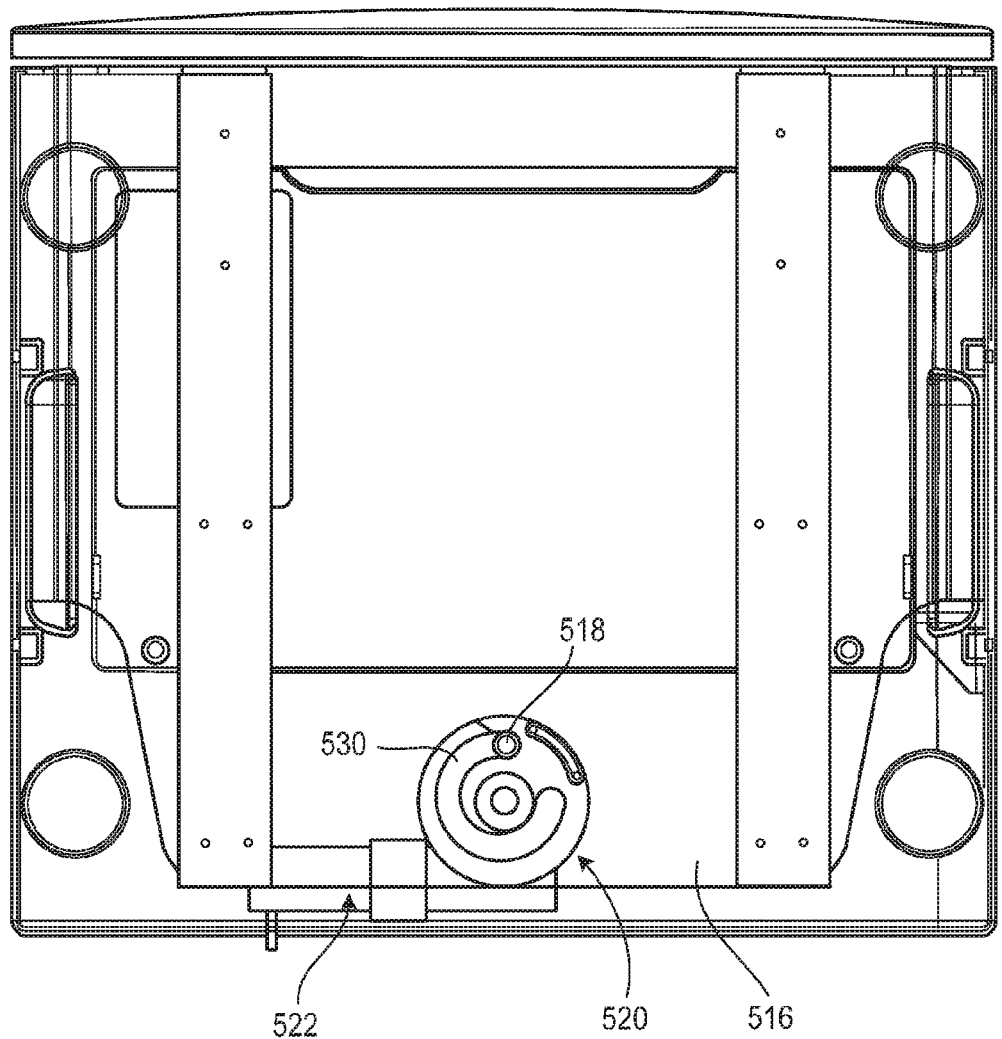
FIGS. 20 and 21 are top schematic views of the drawer of the bottom module of the portable hemodialysis system of FIG. 1 in partially closed and fully closed positions, respectively.
Figure 21:
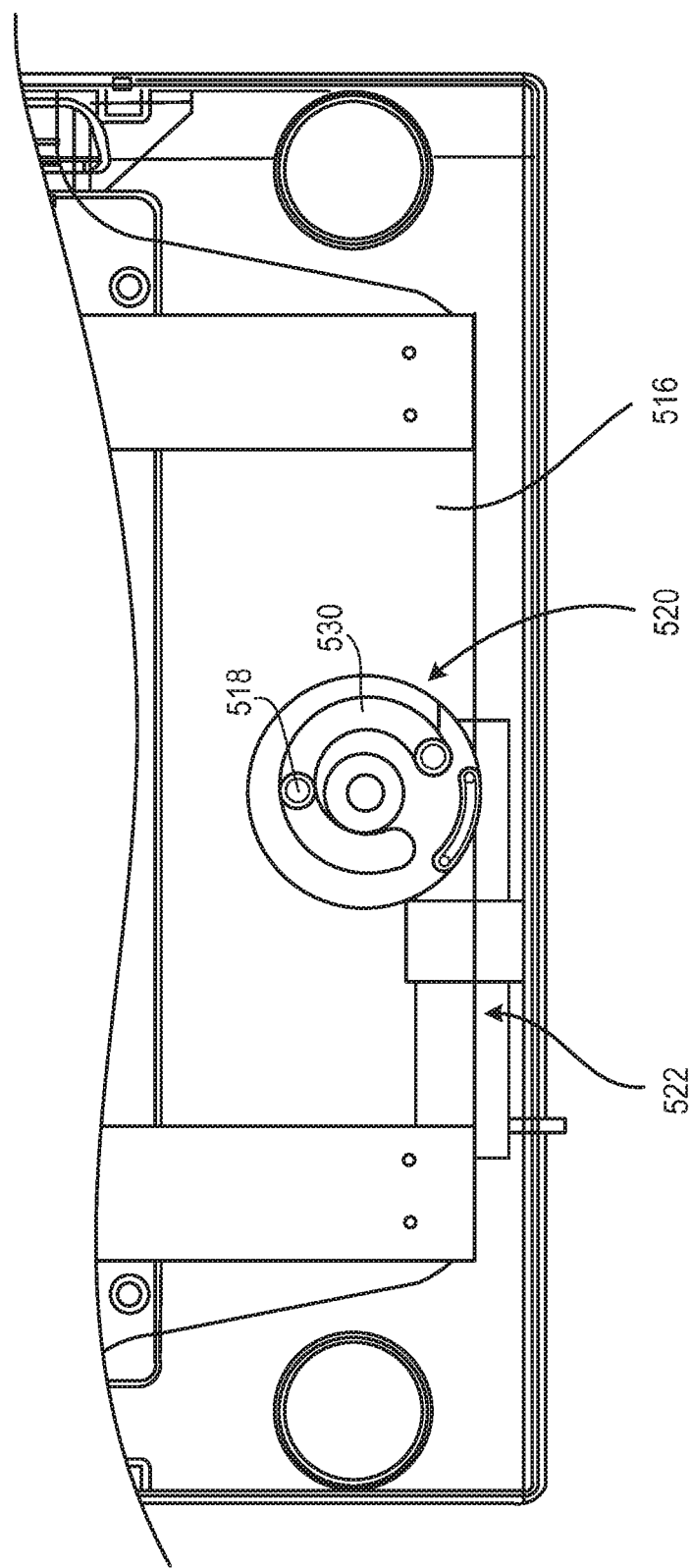

FIGS. 20 and 21 are top schematic views of the drawer 122 in a partially closed and fully closed position, respectively. As shown in FIG. 20, during use, the drawer is closed until the bearing pin 518 of the platen 504 engages the cam 520. The cam 520 forms a spiral slot 530 in which the bearing pin 518 is received. As the bearing pin 518 enters the spiral slot 530, the cam drive 522 is activated, causing the cam 520 to rotate in a clockwise direction. The bottom module 106 can, for example, include an optical interrupter adapted to activate the cam drive 522 when the drawer 122 is sufficiently closed to cause the bearing pin 518 to enter the slot 530. Alternatively or additionally, the bearing pin 518 itself can include a switch that activates the cam drive 522 when the bearing pin 518 enters the slot 530. This switch can, for example, be positioned on the rear surface of the bearing pin 518 such that the switch is activated upon contacting the cam 520.

Referring to FIG. 21, as the cam driver 522 rotates the cam 520 in the clockwise direction, the spiral shape of the slot 530 pulls the bearing pin 518, and thus the pull plate 516, in the rearward direction. The spiral slot 530 of the cam driver 522 can, for example, be designed to pull the bearing pin 518 and the pull plate 516 a distance of about one inch or less in the rearward direction. As the pull plate 516 moves in the rearward direction, the front end regions of the elongate members 506, 508 of the left and right scissor mechanisms move rearwardly, causing the scissor mechanisms to raise the platen 504 and the dialysate component carrier 120 sitting on the platen 504. As the dialysate component carrier 120 is raised, the pump lines 182, 184, 186, 188, 189 come into contact with their associated pumps 238, 240, 242, 244, 245 positioned in the bottom module 106 and the pump lines 182, 184, 186, 188, 189 deflect into the recesses 257 formed by the bottom surface of the drawer 122. Thus, by activating the pumps 238, 240, 242, 244, 245, fluid can be forced through the various fluid lines connected to the dialysate component carrier 120. In addition, raising the dialysate component carrier 120 brings the portions of the fluid lines exposed by the apertures 198, 199, 200 into close proximity with their associated sensors 246, 250, 254, and brings the pressure and ammonium sensor capsules 204, 206 into close proximity with the pressure and ammonium sensors 248, 252. This arrangement permits accurate measurements related to various different properties of the fluids flowing through those fluid lines. The segments of the fluid lines underlying the aperture 202 are similarly brought into close proximity to the heater 256 to allow the heater 256 to warm the fluids passing though those lines to a desired temperature and then to maintain those fluids within a desired temperature range.

To open the drawer 122 after treatment, the user can press a button on a control panel (e.g., a touch screen) of the hemodialysis machine that causes the cam drive 522 to rotate the cam 520 in a counterclockwise direction, and thus to move the bearing pin 518 and the pull plate 516 toward the front of the machine. This rotation of the cam 520 causes the drawer 122 to move into a slightly open position. The user can then manually open the drawer 122 to the fully open position. In some implementations, the bottom module 106 is equipped with a hand crank that permits the user to manually rotate the cam 520 in the event of a power loss to the machine. The hand crank can, for example, extend from the rear surface of the machine.

In certain implementations, the drawer 122 includes one or more springs to assist with lowering the scissor mechanisms. The drawer 122 can, for example, include one or more springs that are secured to the front region of the pull plate 516 and to the front face of the drawer 122 to apply a forward force to the pull plate 516. Alternatively or additionally, the drawer 122 can include one or more springs secured at one and to the base 510 of the drawer 122 and at the other end to the platen 504 to apply a downward force to the platen 504.

Referring again to FIGS. 1 and 2, the sorbent device 124 includes a housing containing a sorbent cartridge capable of removing uremic toxins. In some implementations, the cartridge is disposable. The cartridge can, for example, be constructed such that it can be disposed after use and removed from the housing. The replaced cartridge could then be replaced with a similar cartridge for a subsequent use of the system 100. The cartridge can purify water and regenerate spent dialysis solution through the use of a series of layers which can remove heavy metals (e.g., lead, mercury, arsenic, cadmium, chromium and thallium), oxidants (e.g., chlorine and chloramine), urea, phosphate and other uremic waste metabolites (e.g., creatinine and uric acid) from the solution, without removing or adsorbing excessive amounts of cations (e.g., calcium, magnesium, sodium, potassium) or essential ions.

In some implementations, the components of the cartridge that perform the afore-mentioned functions include a purification layer that includes activated carbon; an ion exchange layer that includes a polymer phosphate binder or an ion exchange sorbent; and a urea removal layer that includes strong acid cation exchange resin and basic resin(s) or urea-degrading enzymes and an ion exchange sorbent together with a composition that rejects cations (e.g., flat membrane/hollow fibers described further herein, an ion-exchange membrane, or an encapsulation surrounding the urea removal components).

In certain implementations, the cartridge includes the following layers and materials: sodium zirconium carbonate or other alkali metal-Group IV metal-carbonate; zirconium phosphate or other ammonia adsorbents; alumina or other like material; alumina supported urease or other immobilized enzyme layer or other material to convert urea to ammonia, such as diatomaceous earth or zirconium oxide; and granular activated carbon, such as charcoal, or other adsorbent. The sodium zirconium carbonate component can act as a phosphate adsorbent. The zirconium oxide can be capable of acting as a counter ion or ion exchanger to remove phosphate, and can be in the form of hydrous zirconium oxide (e.g., hydrous zirconium oxide containing acetate). The zirconium oxide can also be blended with the sodium zirconium carbonate when positioned in the cartridge.

Non-limiting examples of urea-degrading enzymes that can be employed in either implementation of the sorbent cartridge include enzymes that are naturally occurring (e.g. urease from jack beans, other seeds or bacteria), produced by recombinant technology (e.g., in bacterial, fungal, insect or mammalian cells that express and/or secrete urea-degrading enzymes) or produced synthetically (e.g., synthesized). In some implementations, the enzyme is urease.

In certain implementations, the sorbent cartridge further includes hollow fibers. The hollow fibers can reject positively charged ions, as well as increase the capacity of the cartridge. The hollow fibers can be coated with an ion-rejecting material, which through a water-purification like mechanism allows the urea through but rejects positively charged ions such as calcium and magnesium. The material coating the hollow fibers can be any such material known to one of skill in the art (e.g., fatty acids or polymer chains like polysulfone) that can effectively reject calcium and magnesium and therefore retain the ions in the dialysis solution. Generally, to have this effect the material itself would be positively charged. In some implementations, for example, the material used to coat the hollow fibers is cellulose acetate (e.g., cellulose triacetate). The hollow fibers that are to be coated are commercially available (e.g., Fresenius Medical Care North America) and can be coated with any desired ion-rejecting material available to one having skill in the art.

Alternatively, the hollow fibers can include an ion-selective nanofiltration membrane. Such membranes are commercially available from a number of sources (e.g., Amerida, Koch, GE, Hoechst and Dialyzer outletw Chemical). These membranes have pores sizes that prevent ionic substances from diffusing through the membrane. For example, there are nanofiltration membranes that have an ability to reject ions with more than one negative charge (e.g., sulfate and phosphate) while allowing single-charged ions to pass through, with the converse also being the case. In either case, the hollow fiber devices are available in a variety of dimensions and need only be small enough to fit in the replaceable cartridge, which can be sized for use in an in-home system.

In certain implementations, the sorbent cartridge can further include a flat membrane that is covered with a positively charged material like those described above. In addition, the membrane can be an ion exchange (e.g., anion) membrane that limits the passage of positively charged ions (e.g., Astrom® Neosepta® AFX anion exchange membrane, PCA GmbH PC-SA anion exchange membrane). Advantageously, this ion exchange membrane also has an ability to adsorb phosphate.

The cartridge and/or its components or layers can be replaced (e.g., membrane, urea-degrading enzyme), regenerated (e.g., resin, sorbent) and/or sterilized for re-use when necessary (e.g., saturation, damage, depletion). In addition, the entire sorbent device can be replaceable and thus removed from the dialysis system when there is a decrease in the regeneration efficiency of the cartridge (e.g., through layer saturation) or the cartridge becomes worn or damaged, for instance.

Further examples of sorbent devices are described in U.S. Pat. No. 6,878,283; U.S. Pat. No. 7,033,498; and in Sorb's REDY cartridge (e.g., see "Sorbent Dialysis Primer" COBE Renal Care, Inc. Sep. 4 1993 Edition, and "Rx Guide to Custom Dialysis" COBE Renal Care Inc. Revision E. September 1993), all incorporated in their entirety by reference herein.

Typically, the hemodialysis machine 102 is a reusable device while the blood and dialysate component carriers 108, 120 and all of their associated components are disposable (i.e., constructed for single use). Referring again to FIGS. 1 and 2, to prepare the system 100 for treatment, the scales 168, 170 are extended from the top module 104, as shown in FIGS. 1 and 2. The sorbent device 124 and the dialysate reservoir 126 are then positioned on their scale 168. At this point, the sorbent device 124 and the dialysate reservoir 126 are dry (i.e., not filled with liquid). The dilution water container 172 is then filled with tap water, and the sodium chloride solution container 174 is filled with sodium chloride solution. The sodium chloride solution can, for example, be made by mixing sodium chloride powder with tap water in the container. After filling the dilution water container 172 and the sodium chloride solution container 174, those containers are placed on the other scale 170.

After positioning the sorbent device 124, the dialysate reservoir 126, the dilution water container 172, and the sodium chloride solution container 174 on their respective scales 168, 170, the blood component carrier 108 is secured to the top module 104. The blood component carrier 108 is usually supplied to the user in a closed, sterile bag. Thus, the user removes the blood component carrier 108 from its sterile bag before securing it to the top module 104. The U-shaped blood pump line 140 is operatively engaged with the blood pump 156 by wrapping the blood pump line 140 around the blood pump 156. The drug line 154 leading from the blood circuit is then connected to the heparin vial 166, and a portion of the drug line 154 downstream of the vial is operatively engaged with the drug pump 164. In particular, the drug line 154 is positioned within a slot formed by the housing of the drug pump 164 such that the drug line 154 is compressed against the rolling members of the peristaltic drug pump 164.

With the blood component carrier 108 secured to the top module 104 and the various blood lines attached to their associated devices, the door 110 of the top module 104 is closed and the inflatable pad within the door 110 is inflated. This compresses the blood component carrier 108 and its components between the door 110 and the front face 112 of the top module 104 such that the pressure sensors 158, 160 (shown in FIG. 5) in the top module 104 are brought into close proximity to the pressure sensor capsules 134, 136 secured to the blood component carrier 108 and the level detector 162 (shown in FIG. 5) is brought into close proximity to the air release chamber 132 secured to the blood component carrier 108.

The drawer 122 of the bottom module 106 is then opened and the dialysate component carrier 120 is inserted into the drawer 122. Similar to the blood component carrier 108, the dialysate component carrier 120 is usually supplied to the user in a closed, sterile bag. Thus, the user removes the dialysate component carrier 120 from its sterile bag before placing it within the drawer 122. As discussed above, using the locating pins extending from the inner surface of the drawer 122, the dialysate component carrier 120 is positioned within the drawer 122 such that the pumps, sensors, and heater of the bottom module 106 align with their associated apertures and fluid lines of the dialysate component carrier 120 when the drawer 122 is closed. After positioning the dialysate component carrier 120 within the drawer 122, the drawer 122 is closed and the sorbent device inlet line 216 and the dialysate reservoir outlet line 220 are fluidly connected to the sorbent device 124 and the dialysate reservoir 126, respectively. The dilution water line 229 and the sodium chloride solution line 231 are similarly inserted into the dilution water container 172 and the sodium chloride solution container 174, respectively, and connected to the dilution water/sodium chloride solution outlet line 230 via the three-way valve 232. The sorbent device inlet line 216 is connected to the fluid fitting at the bottom of the sorbent device 124. The dialysate reservoir outlet line 220 is inserted into the dialysate reservoir 126 such that the open end of the line 220 is positioned near the bottom of the dialysate reservoir 126 and submerged in the dialysate therein. In addition, the connector line 128 is connected to the fluid fittings at the top of the sorbent device 124 and the dialysate reservoir 126 to place the sorbent device 124 and the dialysate reservoir 126 in fluid communication with one another.

With the blood component carrier 108 secured to the top module 104 and the dialysate component carrier 120 contained within the drawer 122 of the bottom module 106, the user fills the fill/drain container 228 with tap water and powdered dialysate concentrate to make dialysate. To ensure that the powdered dialysate concentrate is adequately mixed with the water, the user can manually shake or stir the solution. The user then connects the fill/drain line 226 of the dialysate component carrier 120 to the fill/drain container 228 by inserting the fill/drain line 226 into the fill/drain container 228 such that the open end of the fill/drain line 226 is positioned near the bottom of the fill/drain container 228 and is submerged in the dialysate. As discussed below, the dialysate is pulled into the dialysate circuit via the fill/drain line 226 by running the ultrafiltrate pump 242 in the bottom module 106 in reverse. Thus, positioning the open end of the fill/drain line 226 near the bottom of the fill/drain container 228 helps to ensure that the open end of the fill/drain line 226 remains below the liquid surface throughout the prime and fill phases of the set up process and is thus able to draw dialysate from the fill/drain container 228 throughout the prime and fill phases, which are described in greater detail below.

The user then fills the infusate jar 233 with tap water and a powdered concentrate (i.e., a calcium, magnesium, and potassium concentrate) to make infusate solution. The user then connects the infusate injection line 235 of the dialysate component carrier 120 to the infusate jar 233 by inserting the infusate injection line 235 into the infusate jar 233 such that the open end of the infusate injection line 235 is positioned near the bottom of the infusate jar 233 and is submerged in the infusate.

After connecting the infusate jar 233 to the infusate injection line 235, a saline bag 258 is connected to the priming line 152, which is fluidly connected to the blood circuit formed by the blood lines. The saline bag 258 is hung from an IV pole extending from the hemodialysis machine 102. The saline bag 258 can alternatively be hung from a separate IV pole positioned next to the system 100.

While the steps of preparing the system 100 for treatment have been described as being performed in a particular order, it should be understood that the order of the steps can be changed in any of various different ways without affecting the treatment.

Figure 11A:
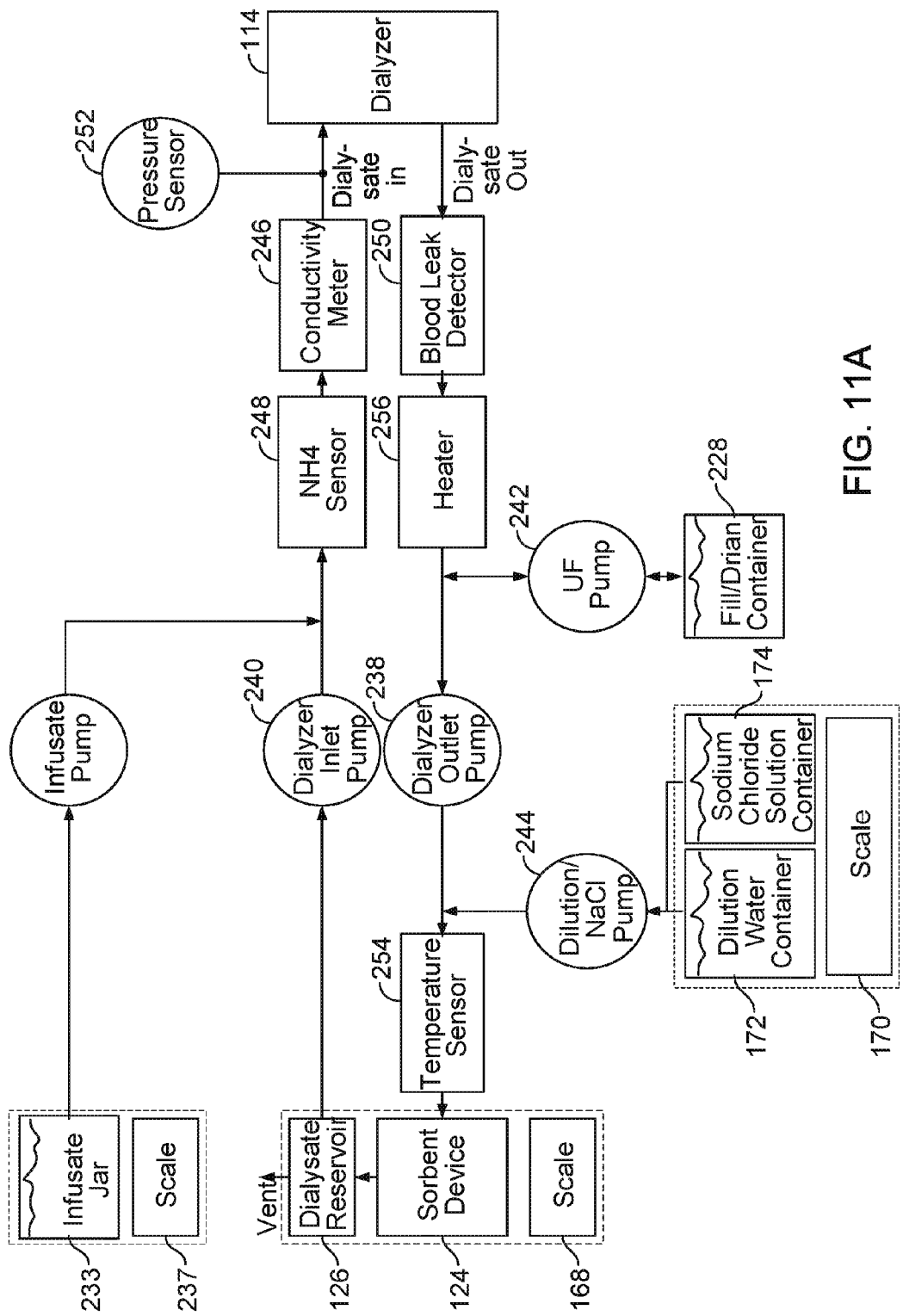
FIGS. 11A and 11B are schematics of fluid flow through the portable hemodialysis system of FIG. 1 during set up.
Figure 11B:
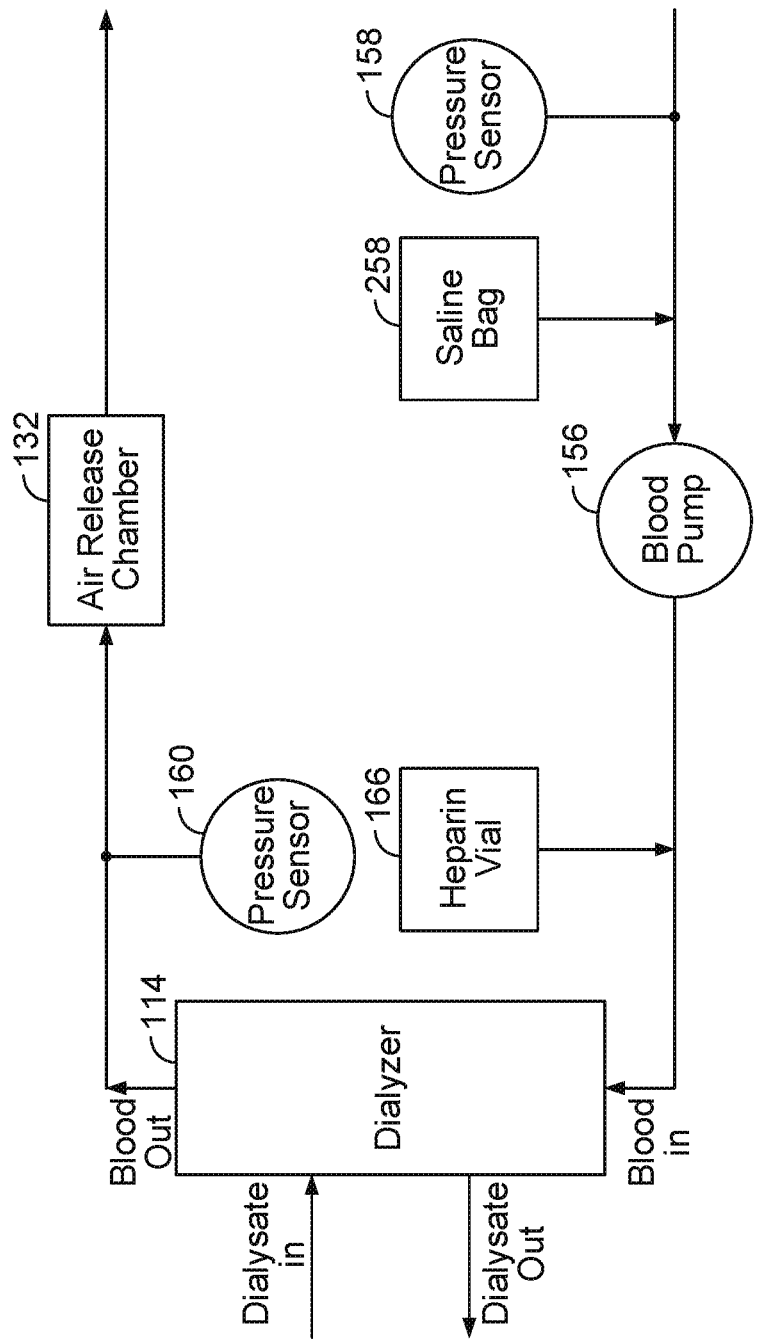

FIGS. 11A and 11B are schematics of fluid flow through the dialysis system 100 during set up. Referring to FIGS. 1, 2, and, 11A, to ready the dialysate within the fill/drain container 228 for treatment, the ultrafiltrate pump 242 in the bottom module 106 of the hemodialysis machine 102 is operated in reverse to draw dialysate from the fill/drain container 228 into the dialysate circuit where it is warmed and circulated. Within the dialysate circuit, the dialyzer outlet pump 238 and the dialyzer inlet pump 240 are used to circulate the dialysate through the sorbent device 124, the dialyzer 114, and the various other dialysate components and lines therebetween. As the dialysate passes through the sorbent device 124, certain substances, such as calcium, magnesium, potassium, and sodium are removed from the dialysate. As discussed above, the sorbent device 124 is also adapted to remove toxins, such as urea, from fluid flowing therethrough. However, the dialysate from the fill/drain container 228 would generally not contain any urea at this point as it has not yet been exposed to the patient's blood.

Upon exiting the top of the sorbent device 124, the dialysate flows into the dialysate reservoir 126. The dialysate reservoir 126 is vented (i.e., open to the atmosphere) and thus helps to ensure that gases within the dialysate are released. As dialysate is being introduced into the dialysate reservoir 126 via the connector line 128 that is connected to the fluid fittings at the top of the sorbent device 124 and the dialysate reservoir 126, dialysate is also drawn from the dialysate reservoir 126 by the dialyzer inlet pump 240 via the dialysate reservoir outlet line 220. At this stage of the process, the dialyzer inlet pump 240 can be operated at a slower speed than the dialyzer outlet pump 238 in order to fill the dialysate reservoir 126 to a desired level with dialysate. In some implementations, the dialyzer inlet pump 240 remains deactivated until the dialysate reservoir 126 is filled to the desired level with dialysate. The microprocessor of the hemodialysis machine 102 controls the pumps 238, 240 based on the volume of dialysate determined to be in the dialysate reservoir 126. The microprocessor can, for example, operate the pumps in a manner to fill the dialysate reservoir 126 until the scale 168 indicates that the dialysate reservoir 126 contains the desired volume of dialysate. After the dialysate reservoir 126 is filled with the desired volume of dialysate, the dialyzer inlet pump 240 and the dialyzer outlet pump 238 are operated at substantially the same speed to achieve circulation of the dialysate within dialysate circuit at a substantially constant flow rate.

As the dialysate is pumped through the dialyzer inlet line 222 by the dialyzer inlet pump 240, a desired amount of infusate solution, which includes magnesium, calcium, and potassium, is pumped into the dialyzer inlet line 222 from the infusate jar 233 by activating the infusate pump 245. The microprocessor controls the infusate pump 245 based on the dialysate flow. The infusate can, for example, be infused at $1/342$ of the dialysate flow to maintain physiological infusate levels. The infusate jar scale 237 is used to measure the amount of infusate delivered. The microprocessor can confirm that the infusate pump 245 is delivering the desired amount of infusate by monitoring the weight of the infusate jar 233.

The dialysate then passes across the ammonium sensor 248, which detects ammonium levels within the dialysate. The microprocessor is connected to the ammonium sensor 248 and receives data regarding ammonium levels within the dialysate. The ammonium sensor 248 can help to determine the state of the sorbent device 124. As the sorbent device 124 is used to recycle spent dialysis, the ammonium levels in the dialysate will increase. Upon reaching a maximum acceptable ammonium level, the treatment can be terminated by the microprocessor. Alternatively, upon reaching the maximum acceptable ammonium level, the microprocessor can cause a warning signal (e.g., an audible and/or visual signal) to be emitted. This signal can alert the user to replace the spent sorbent device with a fresh sorbent device before resuming treatment. If the ammonium levels within the dialysate are within an acceptable range, as would be expected at this early stage of the process, the pumps continue to circulate the dialysate through the dialysate circuit.

The dialysate, after passing the ammonium sensor 248, passes by the conductivity meter 246. The conductivity meter 246 sends a signal regarding the measured conductivity to the microprocessor, which can estimate, based on the measured conductivity, the concentration of sodium within the fluid. The dilution water/sodium chloride solution pump 244 and the three-way valve 232 in the lines leading from the sodium chloride solution container 174 and the dilution water container 172 are then activated by the microprocessor in a manner to introduce sodium chloride solution into the sorbent device inlet line 216 from the sodium chloride solution container 174 if the conductivity reading indicates that the sodium level in the dialysate is lower than desired, or to introduce dilution water into the sorbent device inlet line 216 from the dilution water container 172 if the conductivity reading indicates that the sodium level in the dialysate is higher than desired. The dilution water can be metered into the sorbent device inlet line 216 by activating the dilution water/sodium chloride solution pump 244 and manipulating the three-way valve 232 to allow flow from the dilution water container 172 but prevent flow from the sodium chloride solution container 174. Similarly, the sodium chloride solution can be metered into the fluid line by activating the dilution water/sodium chloride solution pump 244 and manipulating the three-way valve 232 to allow flow from the sodium chloride solution container 174 but prevent flow from the dilution water container 172. The number of revolutions of the dilution water/sodium chloride solution pump 244, which is a peristaltic pump, can be controlled to deliver a desired volume of sodium chloride solution or dilution water to the dialysate circuit. The scale 170 on which the dilution water container 172 and the sodium chloride solution container 174 are positioned can be used to confirm that the desired volume of sodium chloride or dilution water was delivered to the dialysate circuit.

Prior to reaching the dialysate circuit, the infusate solution, the dilution water, and the sodium chloride solution pass through fluid detectors (e.g., bubble detectors), which can detect the presence or absence of fluid. In the event that no fluid is detected, a signal to that effect is sent to the microprocessor and, in response, the system 100 is shut down and/or an alarm (e.g., an audible and/or visual alarm) is activated to inform the user that the infusate jar 233, the dilution water container 172, or the sodium chloride solution container 174 needs to be refilled.

After passing the conductivity meter 246, the dialysate passes across the pressure sensor 252. The pressure sensor 252 can be used to detect leaks or other anomalies within the dialysate circuit. For example, a pressure reading that is below an acceptable minimum value can indicate a leak within the dialysate circuit, and a pressure reading above an acceptable maximum limit can indicate a kinked line or an obstruction within a line. Upon detecting a pressure outside an acceptable range, the pressure sensor 252 transmits a signal to the microprocessor, which shuts down the system 100 and/or provides an indication (e.g., an audible and/or visual indication) to the user.

After passing by the pressure sensor 252, the dialysate passes through the dialyzer 114. Because the arterial and venous patient lines 116, 118 are not connected to the patient at this stage of the process, no blood is flowing through the dialyzer 114. Thus, the composition of the dialysate exiting the dialyzer 114 is substantially unchanged relative to the dialysate entering the dialyzer 114.

After exiting the dialyzer 114, the dialysate passes by the blood leak detector 250, which detects whether blood has leaked into the dialysate via the dialyzer 114.

As the dialysate flows through the dialyzer outlet line 208 after passing the blood leak detector 250, the heater 256 within the bottom module 106 of the hemodialysis machine 102 heats the dialysate. The dialysate, after passing under the heater 256, is pumped back toward the sorbent device 124 by the dialyzer outlet pump 238. Before reaching the sorbent device 124, the dialysate passes through the temperature sensor 254, which detects the temperature of the dialysate and transmits a signal regarding the temperature of the dialysate to the microprocessor. The microprocessor controls the heater 256 based on the feedback from the temperature sensor 254. For example, upon reaching a desired temperature, the heat emitted by the heater 256 can be reduced to merely maintain the dialysate at the desired temperature.

The ultrafiltrate pump 242 continues to pull the dialysate from the fill/drain container 228 until a desired volume of dialysate (e.g., about four to six liters of dialysate) is circulating within the dialysate circuit. In order to determine the volume of dialysate delivered to the dialysate circuit from the fill/drain container 228, the microprocessor monitors the number of revolutions of the ultrafiltrate pump 242. In particular, because the ultrafiltrate pump 242 is a metering pump (i.e. a peristaltic pump), the desired volume of dialysate can be delivered to the dialysate circuit by turning the ultrafiltrate pump 242 a number of revolutions that corresponds to that volume. After the desired volume of dialysate has been delivered to the dialysate circuit, the ultrafiltrate pump 242 is turned off and the dialysate is circulated within the dialysate circuit by the dialyzer inlet pump 240 and the dialyzer outlet pump 238.

Now referring to the blood circuit side of FIG. 11B, in addition to drawing dialysate into the dialysate circuit, saline is pulled from the saline bag 258 into the blood circuit formed by the blood lines and other blood components of the blood component carrier 108. As an alternative to or in addition to using a pulling force to draw the saline into the blood circuit, a dedicated saline pump can be used to pump the saline into the blood circuit. Such a pump can be used to automatically deliver a desired volume (e.g., 200 ml, 300 ml, 400 ml) of the saline into the blood circuit. Because the arterial and venous patient lines 116, 118 are not connected to a patient, the saline passes through the blood circuit and out of the open ends of the arterial and venous patient lines 116, 118. As a result, any air that might have been contained within the blood circuit (i.e., within the blood lines and blood components secured to the blood component carrier 108) is forced out of the blood circuit.

Figure 12A:
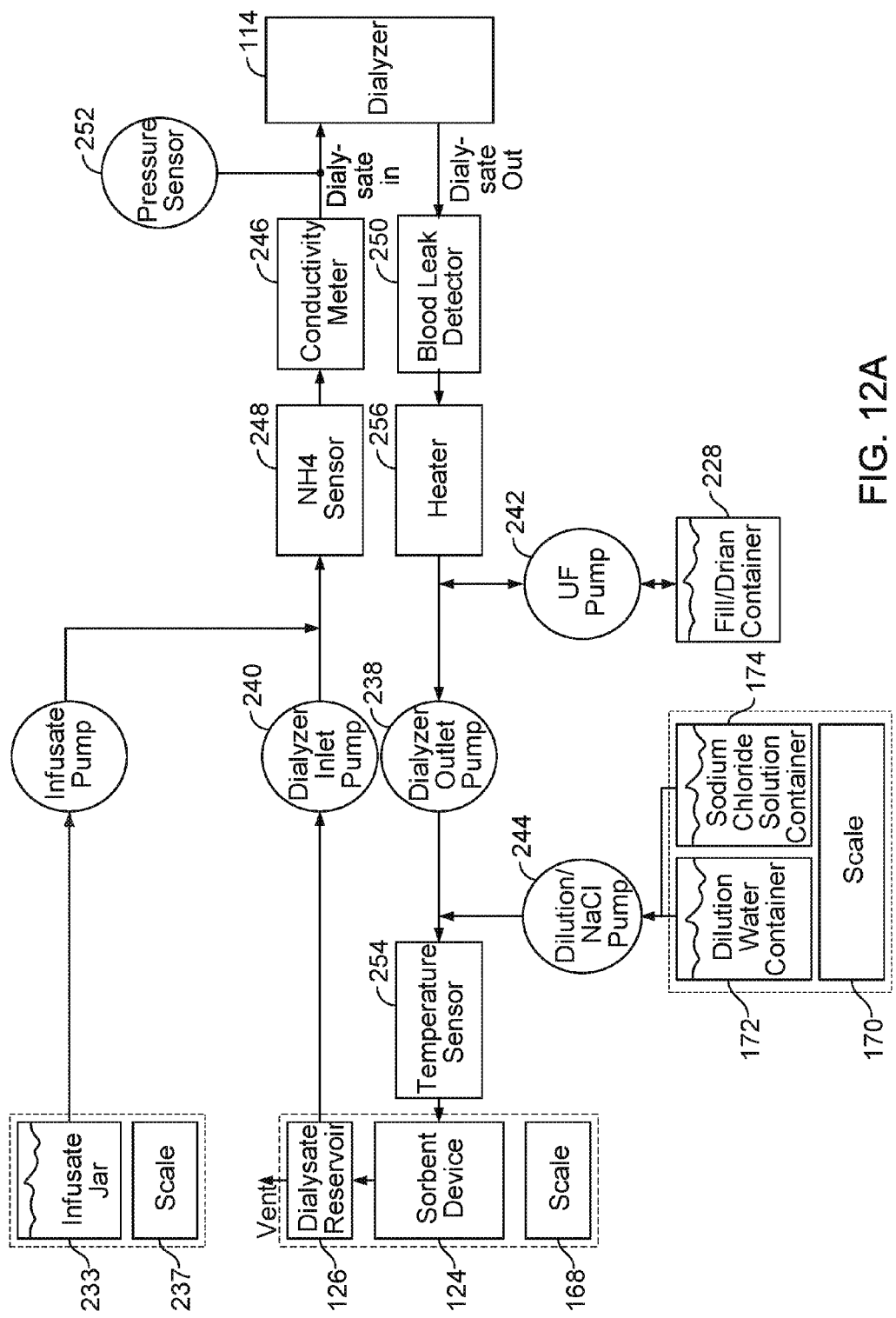
FIGS. 12A and 12B are schematics of fluid flow through the portable hemodialysis system of FIG. 1 during hemodialysis.
Figure 12B:
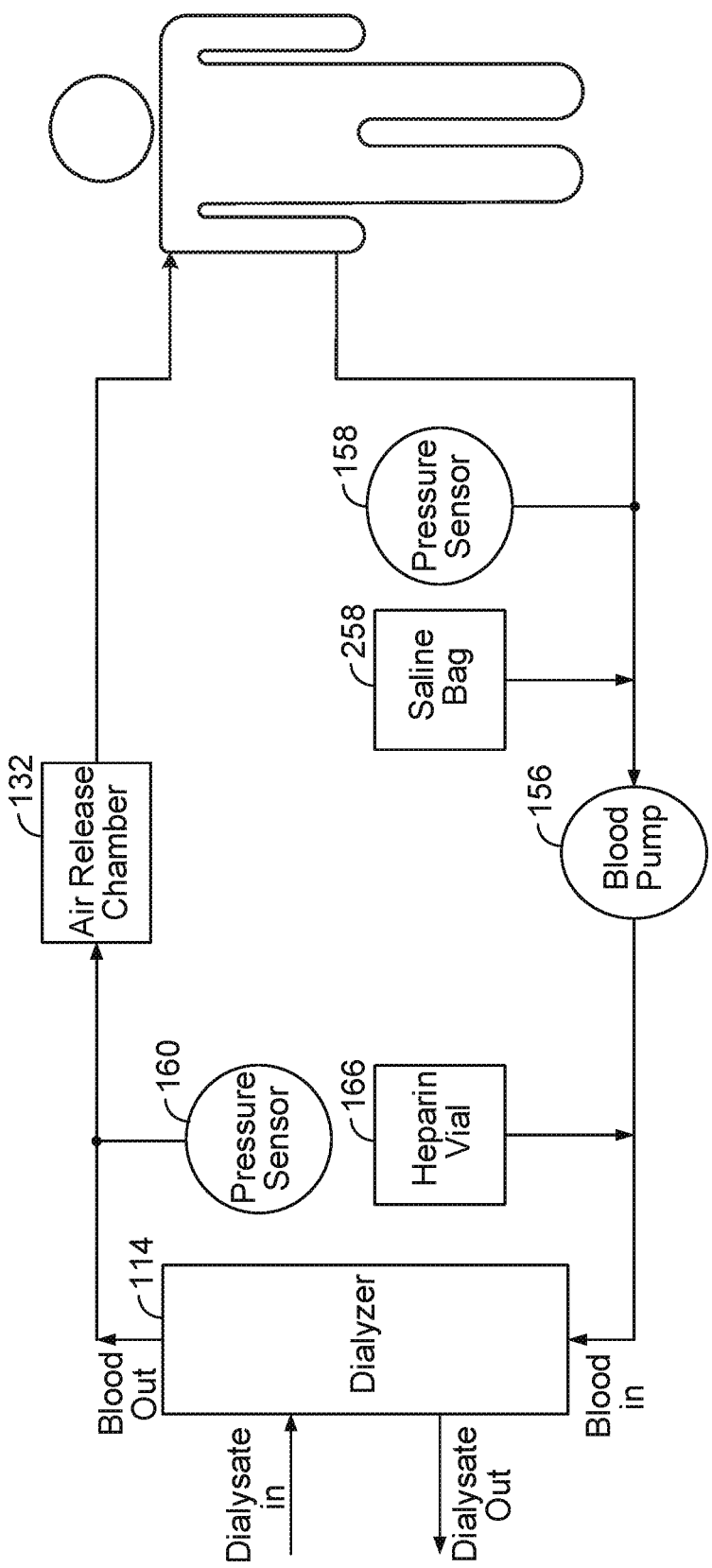

FIGS. 12A and 12B are schematics of fluid flow through the dialysis system 100 during hemodialysis. After flushing the air out of the blood circuit and warming the circulating dialysate to a desired temperature, the arterial and venous patient lines 116, 118 are connected to the patient and hemodialysis is initiated. During hemodialysis, blood is circulated through the blood circuit (i.e., the blood lines, the various blood components, and the dialyzer 114). At the same time, dialysate is circulated through the dialysate circuit (i.e., the dialysate lines, the various dialysate components, and the dialyzer 114).

Focusing first on the blood circuit shown in FIG. 12B, during hemodialysis, the blood pump 156 is activated causing blood to flow through the blood circuit. The blood is drawn from the patient via the arterial patient line 116 and flows to the pressure sensor capsule 134. The pressure sensor 158 on the front face 112 of the top module 104 (shown in FIG. 5) aligns with the capsule 134 and measures the pressure of the blood flowing through the blood circuit on the arterial side. The blood then flows through the U-shaped pump line 140, which is operatively engaged with the blood pump 156. From the pump line 140, the blood flows to the dialyzer 114. After exiting the dialyzer 114, the blood flows through the other pressure sensor capsule 136 where the pressure of the blood on the venous side is measured by the pressure sensor 160 on the front face 112 of the top module 104 (shown in FIG. 5). Next, the blood flows through the entry port of the air release chamber 132 in which any gas, such as air, in the blood can escape. After leaving the air release chamber 132, the blood travels through the venous patient line 118 and back to the patient.

Turning now to the dialysate circuit shown in FIG. 12A, the dialysate passes through the dialyzer 114 at the same time that the patient's blood is passed through the dialyzer 114. As a result, toxins, such as urea, are transferred across a permeable structure (e.g., permeable membrane and/or permeable microtubes) of the dialyzer 114 from the patient's blood to the dialysate. In certain treatments, an ultrafiltration process is also performed to remove excess fluid from the patient's blood. During ultrafiltration, a pressure gradient is created across the permeable structure between the dialysate side and the blood side of the dialyzer 114 by running the ultrafiltrate pump 242. As a result, fluid is drawn across the permeable structure of the dialyzer 114 from the blood to the dialysate. Spent dialysate, including the toxins and excess fluid drawn from the patient, exits the dialyzer 114.

The spent dialysate exiting the dialyzer 114 passes through the blood leak detector 250, which checks to ensure that an unacceptable volume of blood has not leaked through the permeable structure of the dialyzer 114 and into the dialysate. The spent dialysate then passes through the online heater 256, which maintains the temperature of the dialysate within a desired range.

Some of the spent dialysate can be routed to the fill/drain container 228 by activating the ultrafiltrate pump 242 as the spent dialysate is forced through the dialyzer outlet line 208. For example, a volume of the spent dialysate equal to the volume of fluid removed from the patient as a result of the ultrafiltration and the total volume of infusate, sodium, and dilution water added to the dialysate can be pumped to the fill/drain container 228 by the ultrafiltrate pump 242. This can help to ensure that a substantially constant volume of fluid is circulated through the dialysate circuit throughout treatment.

The dialyzer outlet pump 238 forces the volume of the spent dialysate that is not routed to the fill/drain container 228 through the dialyzer outlet pump 238 to the sorbent device 124. As the spent dialysate passes through the sorbent device 124, urea is removed from the spent dialysate. Calcium, magnesium, and potassium are also stripped from the spent dialysate by the sorbent device 124.

The sorbent device 124 is somewhat absorbent and, as a result, the volumetric flow rate of fluid exiting the sorbent device 124 may be slightly less than the volumetric flow rate of fluid entering the sorbent device 124. The tendency of the sorbent device 124 to absorb fluid typically increases as the rate of fluid flow through the sorbent device 124 increases. Upon decreasing the flow rate of fluid through the sorbent device 124, fluid that was previously absorbed by the sorbent device 124 can be released. In such instances, the volumetric flow rate of fluid exiting the sorbent device 124 may be slightly greater than the volumetric flow rate of fluid entering the sorbent device 124.

The recycled dialysate, upon exiting the sorbent device 124, passes through the connector line 128 and into the dialysate reservoir 126. Any gases that may have been produced as a result of chemical reactions within the sorbent device 124 as well as any air that might have been trapped within the recycled dialysate is removed from the recycled dialysate and exits the dialysate reservoir 126 via its vented opening.

The pumping action of the dialysate inlet pump 240 draws the recycled dialysate from the dialysate reservoir 126 into the dialysate reservoir outlet line 220 at a desired volumetric flow rate. Typically, the recycled dialysate is removed from the dialysate reservoir 126 at the same volumetric flow rate at which the spent dialysate enters the sorbent device 124. Thus, even in the event that the volumetric flow rate of the recycled dialysate exiting the sorbent device 124 differs from the volumetric flow rate of the spent dialysate introduced into the sorbent device 124, the volumetric flow rate through the remainder of the dialysate circuit remains substantially constant.

In the manner discussed above, after the recycled dialysate exits the dialysate reservoir 126, the infusate solution is introduced into the recycled dialysate. The recycled dialysate then flows through the ammonium sensor 248. The ammonium sensor 248 can help to determine the state of the sorbent device 124. For example, as the sorbent device 124 is used, the ammonium levels in the dialysate will increase. Upon exceeding an acceptable ammonium level, the treatment can be terminated. Alternatively, upon exceeding the acceptable ammonium level, the sorbent device 124 can be replaced with a fresh sorbent device and treatment can resume.

After exiting the ammonium sensor 248, the recycled dialysate passes through the conductivity meter 246 where the conductivity of the recycled dialysate is measured. Based on the conductivity reading at the conductivity meter 246, sodium chloride solution or dilution water can be added to the dialysate flowing through the sorbent device inlet line 216. In the initial stages of treatment, sodium levels in the recycled dialysate tend to be lower than desired due to the tendency of the sorbent device 124 to strip sodium from fluids passing therethrough. Consequently, in the early stages of the treatment, sodium chloride solution will typically be injected into fluid line to increase the concentration of sodium in the recycled dialysate. In later stages of the treatment, however, the sorbent device 124 may contain high levels of sodium and thus start releasing sodium into the spent dialysate as it passes through the sorbent device 124. This can lead to higher than desired levels of sodium in the recycled dialysate passing through the dialysate reservoir outlet line, resulting in an injection of dilution water into the recycled dialysate.

The recycled dialysate then passes through a pressure sensor 252 that measures the pressure of the recycled dialysate. As discussed above, the measured pressure is sent to the microprocessor and the system 100 is shut down and/or a warning signal (e.g., an audible and/or visual signal) is emitted if the detected pressure falls outside of an acceptable pressure range.

The recycled dialysate then passes through the dialyzer 114 where toxins are transferred from the patient's blood to the dialysate. This process is repeated until the hemodialysis treatment is completed.

After completing the patient's treatment, the dialysate within the dialysate circuit is pumped back to the fill/drain container 228. To do this, the ultrafiltrate pump 242 can be operated at a greater speed than the dialyzer inlet pump 240 and the dialyzer outlet pump 238. The dilution water/sodium chloride solution pump 244 would typically be turned off during this draining phase.

After draining the dialysate circuit, the dialysate component carrier 120 and its components and the various other dialysate components (e.g., the sorbent device 124, the infusate jar 233, the sodium chloride solution container 174, the fill/drain container 228, and their associated fluid lines) are disconnected from the hemodialysis machine 102 and discarded. Similarly, the blood component carrier 108 and it components are disconnected from the hemodialysis machine 102 and discarded. Because all of the components that contact the blood and dialysate during use are disposable, it is typically unnecessary to perform an extensive cleaning operation on the system 100 after use.

Figure 13:
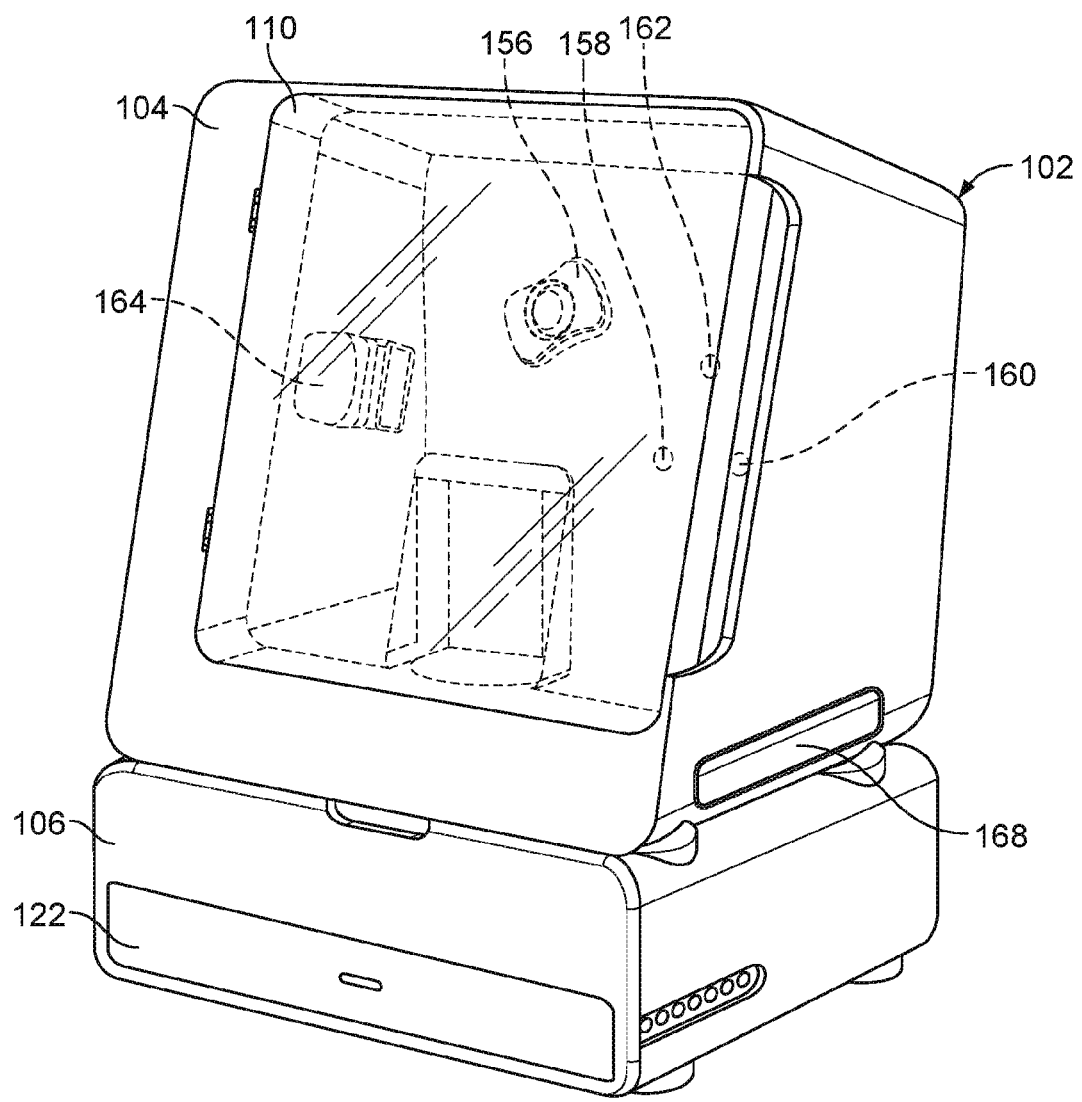
FIG. 13 is a perspective view of the portable hemodialysis system of FIG. 1 configured for transport.

The system 100 can be reconfigured for storage or transport, as shown in FIG. 13. In this configuration, the scales 168, 170 are pushed into the cavity of the top module 104, the door 110 and the drawer 122 are closed, and no dialysate/blood component carriers are connected to the machine 102. In addition, the top module 104 can be removed from the bottom module 106. In this configuration, the system 100 can be easily transported from one place to another. For example, the overall size and weight of the system 100 in this configuration allows a user to place the system 100 in most car trunks or similar spaces for transport.

While certain implementations have been described, other implementations are possible.

Figure 14:
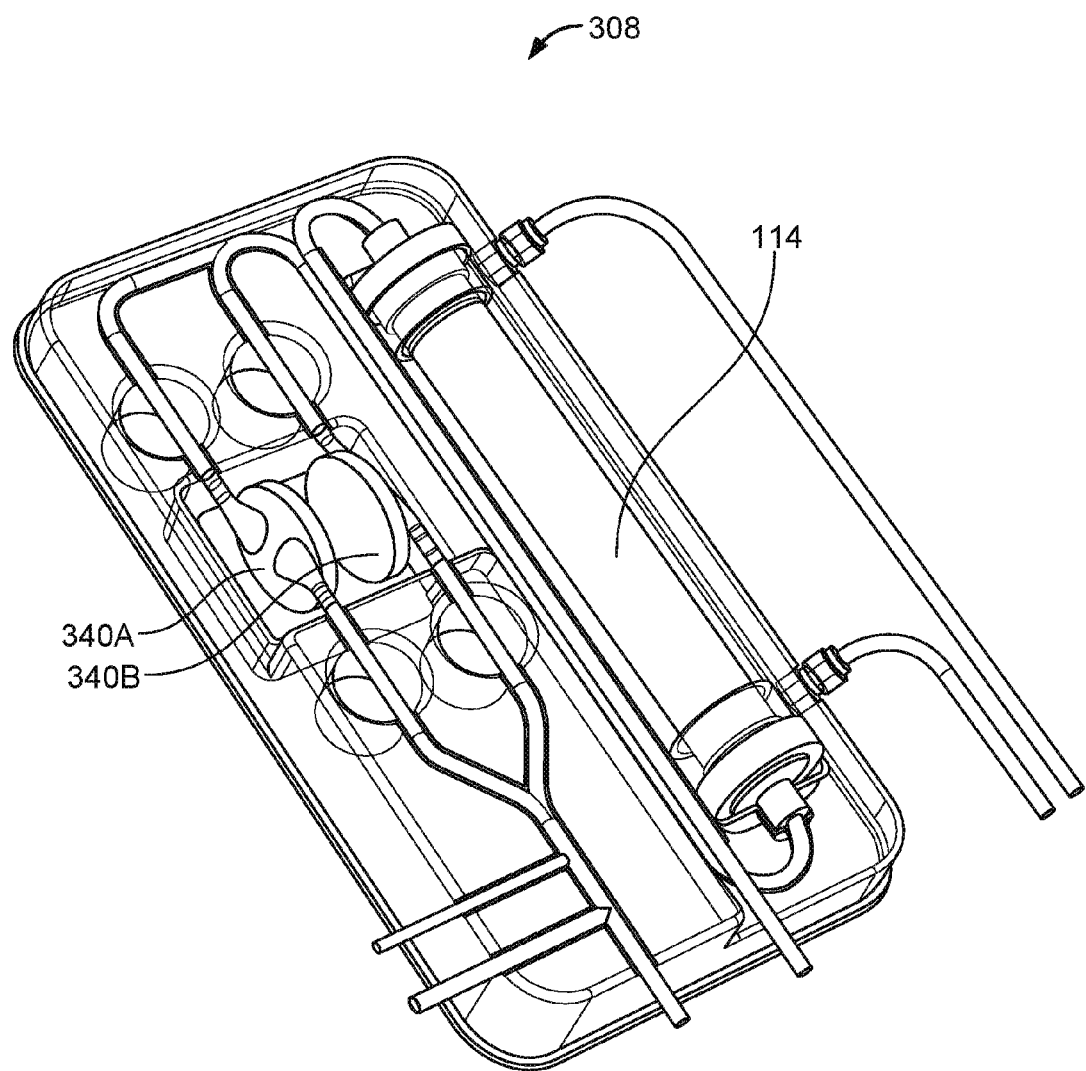
FIG. 14 is a perspective view of another type of blood component carrier that can be used in the portable hemodialysis system of FIG. 1.

While the blood pump 156 has been described as a peristaltic pump, other types of pumps can alternatively or additionally be used. In some implementations, hydraulic or pneumatic pumps are used. FIG. 14 illustrates a blood component carrier 308 that can be used with such pumps. The blood component carrier 308 includes two adjacent diaphragm pumps 340A, 340B secured thereto. Each of the diaphragm pumps includes a housing forming a chamber in which a membrane is disposed. The membrane separates the chamber into first and second sub-chambers. When the blood component carrier 308 is positioned on the front face 112 of the top module of the machine, pressurized fluid sources mate with the diaphragm pumps in a manner such that the fluid sources are fluidly connected to a sub-chamber of each pump. The fluid sources can be activated to deliver pressurized fluid into the sub-chambers and to remove the pressurized fluid from the sub-chambers. As the sub-chambers of the pumps are filled with the pressurized fluid, blood within the other sub-chamber is forced out of the sub-chamber and through the blood lines connected to the carrier. As the pressurized fluid is removed from the sub-chambers (e.g., by vacuum), blood is pulled into the sub-chamber. The pumps are typically operated in an alternating fashion such that one pump expels blood from its chamber as the other pump pulls blood into its chamber and vice versa. This helps to ensure a constant circulation of blood though the blood circuit formed by the blood lines secured to the blood component carrier 308. The pumps can alternatively be operated simultaneously to achieve single needle access. An example of a blood pump of the type described above is the Pulsar Blood Movement System, available from Renal Solutions, Inc. (Warrendale, Pa.).

While the scales 168, 170 have been described as being secured to the bottom surface of the top module 104 via slidable tracks that permit the scales 168, 170 to be extended from the module and stored within a cavity in the module, any of various other mechanisms that allow the scales 168, 170 to be extended from the module and stored within a cavity in the module can be used. Further, while the slidable tracks have been described as being attached to the bottom surface of the top module 104, the slidable tracks or other mechanisms to permit movement of the scales can alternatively or additionally be secured to other surfaces of the top module 104.

While the scales 168, 170 have been described as part of the top module 104, the scales 168, 170 could alternatively be part of the bottom module 106.

While the scales 168, 170 have been described as load cell scales that utilize strain gauges, any of various other types of scales can be used. Other types of scales that can be used include compression load cells, torque load cells, shear beam and double beam load cells, force sensing resistors, pressure transducers, and force sensors.

Figure 15:
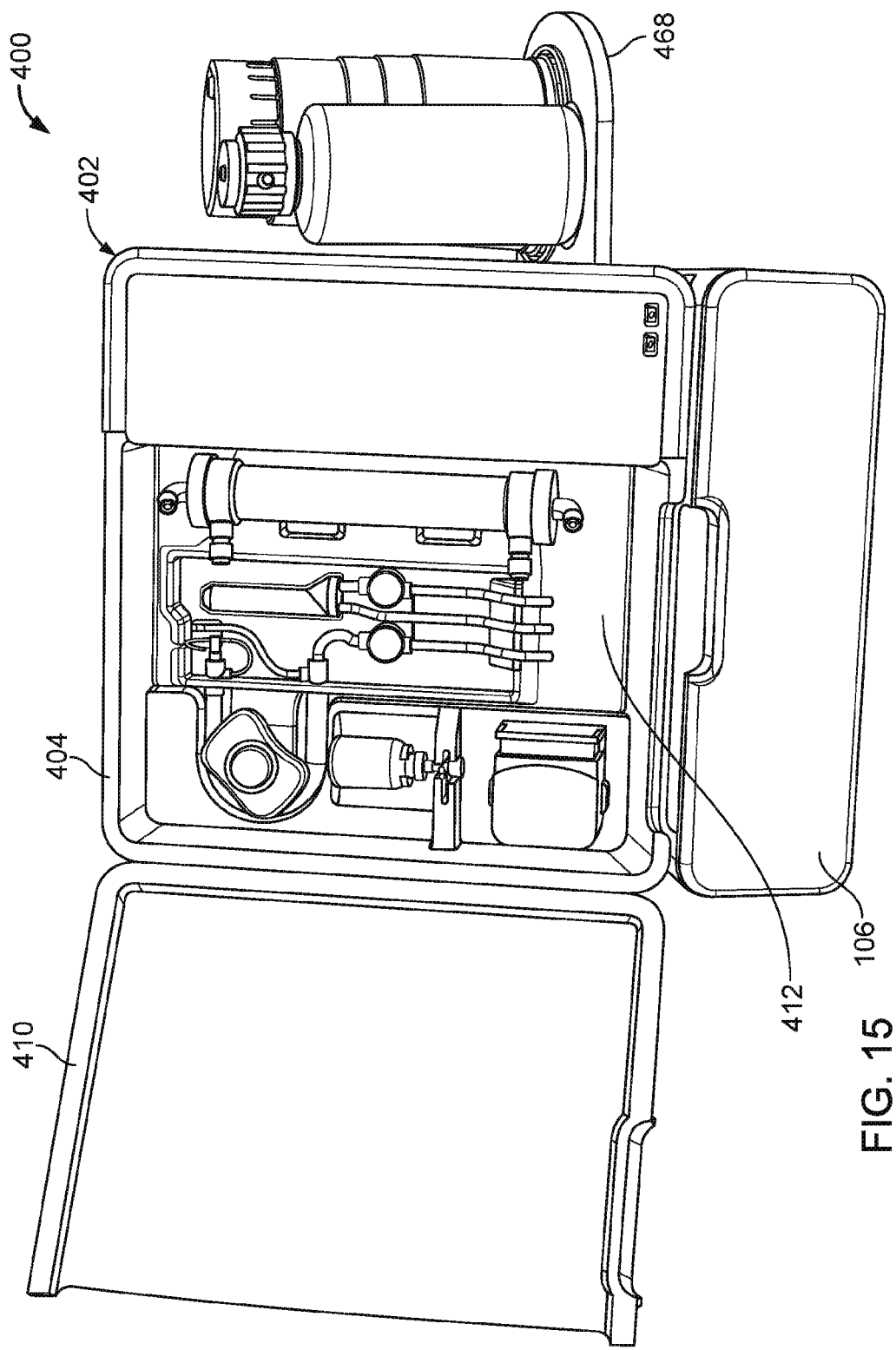
FIG. 15 is a perspective view of a hemodialysis system with a blood component carrier that is fully contained within a carrier compartment of a hemodialysis machine. Foldable weight scales extend from opposite sides of the hemodialysis machine.
Figure 16:
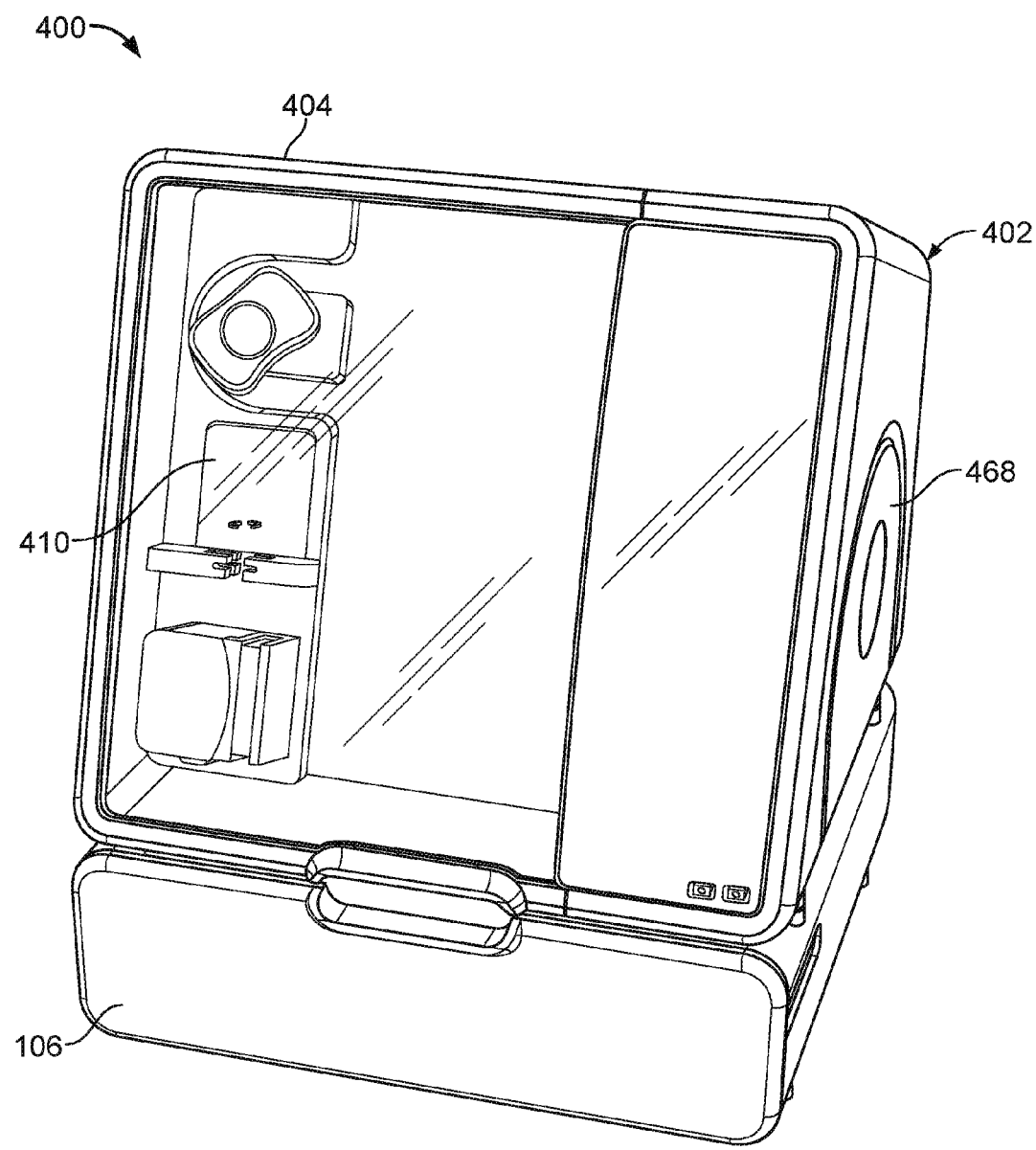
FIG. 16 is a right, perspective view of the hemodialysis system of FIG. 15 in a configuration for transport or storage.
Figure 17:
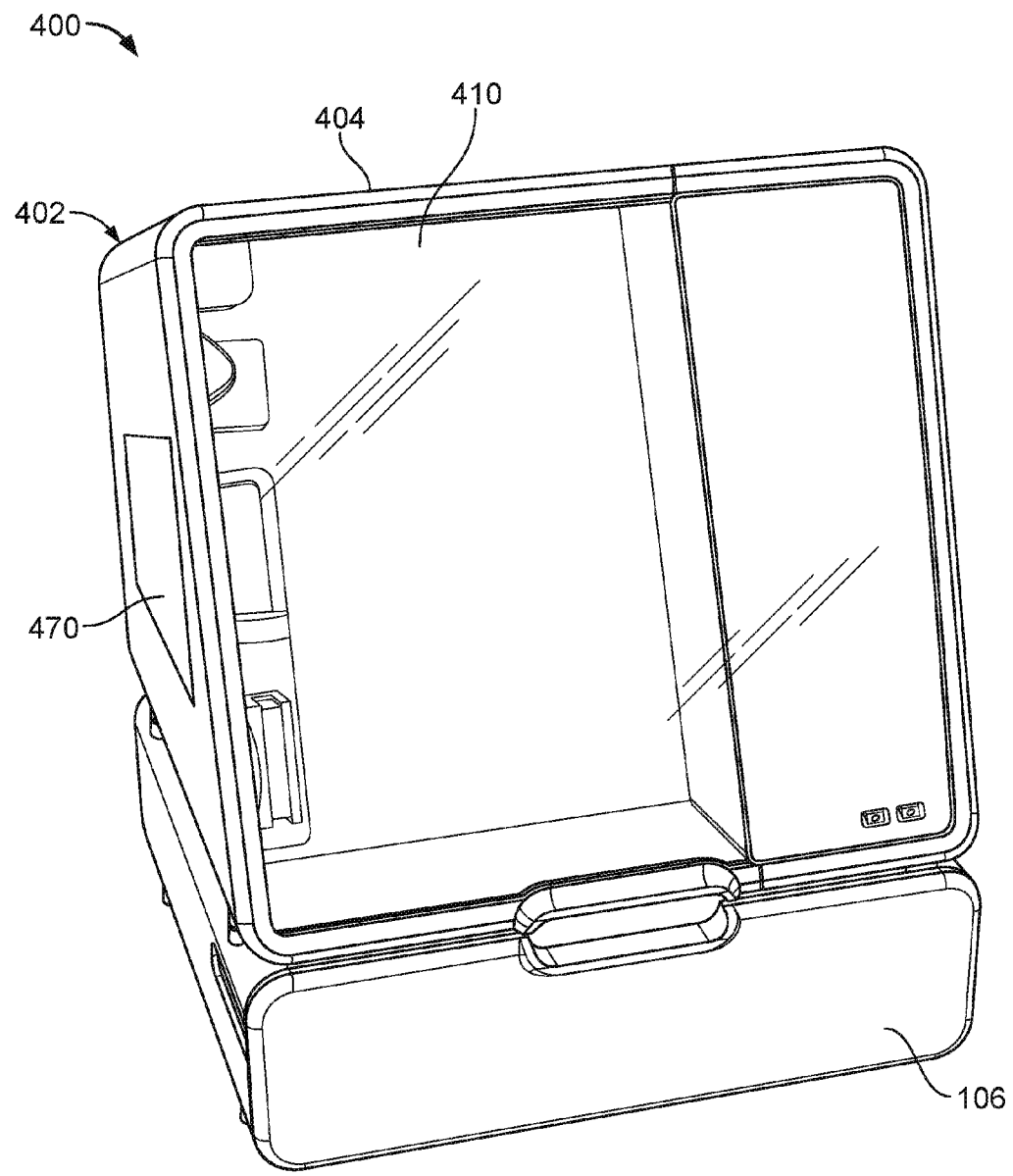
FIG. 17 is a left, perspective view of the hemodialysis system of FIG. 15 in a configuration for transport or storage.

While the dialyzer 114 has been illustrated as extending beyond the side of the hemodialysis machine 102, in certain implementations, the dialyzer is fully contained within a compartment of the hemodialysis machine. In addition, while the scales 168, 170 have been described as being slidable into a cavity formed in the top module 104 of the hemodialysis machine 102 for storage and transport, the scales can alternatively be configured to fold against the side of the hemodialysis machine for storage and transportation. Referring to FIGS. 15-17, for example, a hemodialysis system 400 includes a hemodialysis machine 402 with a top module 404 sitting atop the bottom module 106. The top module 404 includes a door 410 that cooperates with a front face 412 to form a dialysate component carrier compartment that entirely encloses the blood component carrier 108. The top module 404 includes foldable weight scales 468, 470 attached to its opposite side walls. In the storage configuration shown in FIGS. 16 and 17, the weight scales 468, 470 are folded upward against the side walls of the top module 404 to reduce the footprint of the system 400 for transport. The system 400 works in substantially the same way as the system 100 described above.

Figure 22:
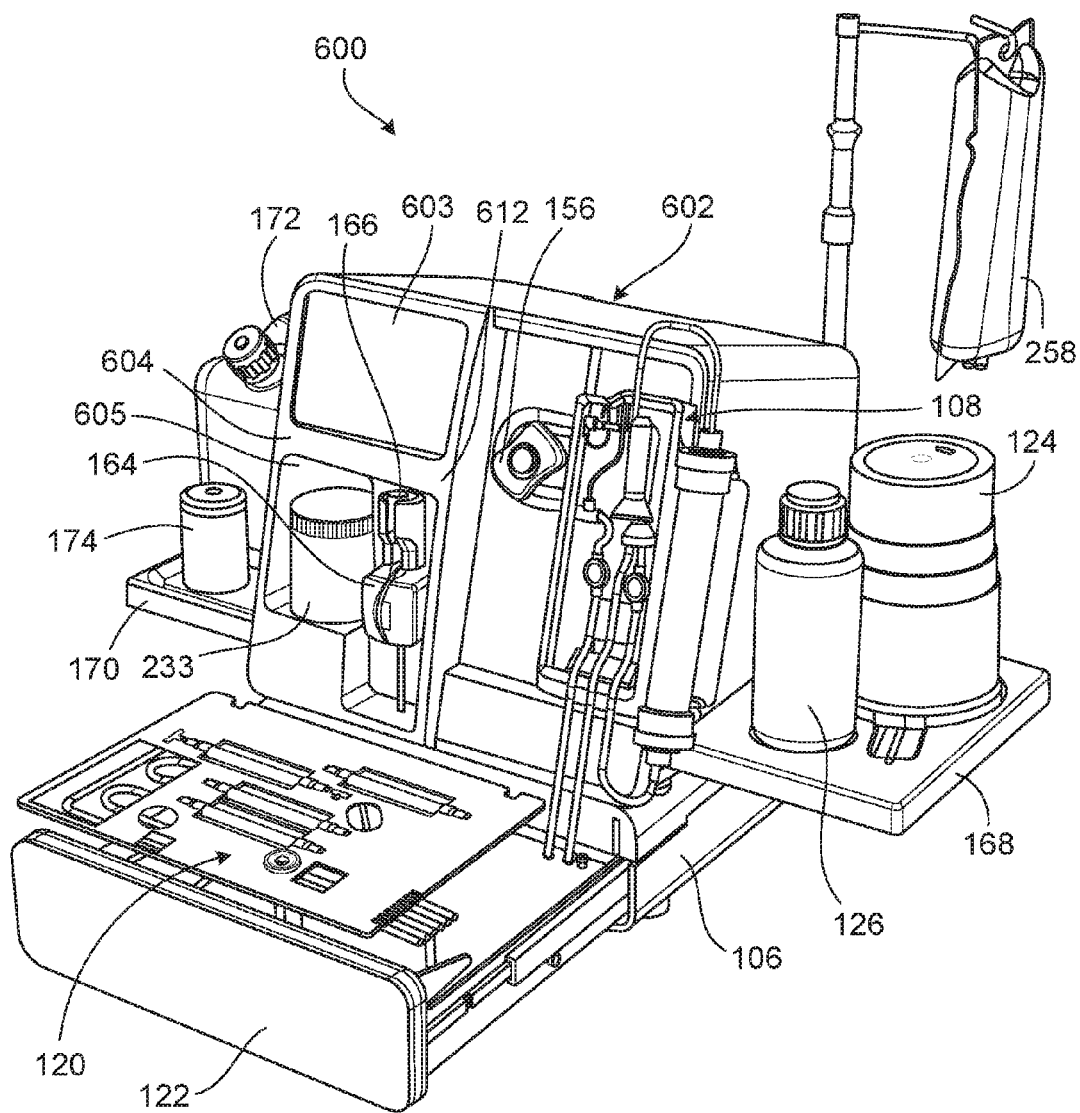
FIG. 22 is a perspective view of a portable hemodialysis system including a hemodialysis machine with a display that can be used as a graphical user interface exposed on its front face.

Various other components of the hemodialysis system can also be configured differently from the configurations in the implementations described above if desired. As shown in FIG. 22, for example, a hemodialysis system 600 includes a hemodialysis machine 602 with a top module 604 that is resting on the bottom module 104 and is equipped with many of the same components as the top module 104 of the hemodialysis machine 102 discussed above. However, some of those components are arranged in a different configuration to accommodate a display (e.g., a touch screen) 603 that is exposed on a front face 612 of the hemodialysis machine 602. The infusate jar 233, the drug vial 166, and the drug pump 164, for example, are situated side-by-side within a recess 605 beneath the display 603. Many of the fluid lines that are used to connect the various different components of the hemodialysis system 600 are not shown in FIG. 22 for simplicity.

The display 603 can be used for a variety of purposes. For example, the display can be used to walk the patient through the set up process and to provide the user with information related to the treatment. The display can also be used to allow the patient to input data and information into the hemodialysis machine 602. In some implementations, the hemodialysis machine 602 is equipped with a web browser and is connected to the Internet such that the patient, via the display 603, can access online records and other information. In certain implementations, the display 603 serves as an interface that allows the patient to communicate with a physician or nurse in order to troubleshoot complications with the hemodialysis machine 602. Apart from the added functionality of the display 603, the hemodialysis system 600 generally operates in the same manner as the hemodialysis system 100 described above.

While the display 603 of the hemodialysis machine 602 has been described as a touch screen that allows the patient to both view and input information, the display 603 can alternatively be a conventional display used for viewing purposes only. In such cases, the front face 612 of the hemodialysis machine 602 is equipped with additional buttons (e.g., hard keys, feather touch buttons, etc.) that allow the patient to navigate through screens displayed on the display 603 and to input data and commands into the hemodialysis machine 602.

While the drawer 122 has been described as including locating pins to ensure that the dialysate component carrier 120 remains in a desired position within the drawer 122, other mechanisms can alternatively or additionally be used. For example, in some implementations, the drawer 122 includes clips or clamps to hold the dialysate component container. Adhesive can also be used to secure the dialysate component carrier 120.

While the dialyzer inlet pump 240, the dialyzer outlet pump 238, the ultrafiltrate pump 242, and the dilution water/sodium chloride solution pump 244 have been described as peristaltic pumps, other types of pumps can alternatively or additionally be used. In some implementations, hydraulic or pneumatic pumps are used. In certain implementations in which hydraulic or pneumatic pumps are used, the dialysate component carrier has a pump arrangement similar to that of the blood component carrier 308 discussed above, with two adjacent diaphragm pumps secured to the carrier body. Each of the diaphragm pumps includes a housing forming a chamber in which a membrane is disposed. The membrane separates the chamber into first and second sub-chambers. When the dialysate component carrier is positioned within the cavity of the drawer and the drawer is closed, pressurized fluid sources mate with the diaphragm pumps in a manner such that the fluid sources are fluidly connected to a sub-chamber of each pump. The fluid sources can be activated to deliver pressurized fluid into the sub-chambers and to remove the pressurized fluid from the sub-chambers. As the sub-chambers of the pumps are filled with the pressurized fluid, dialysate within the other sub-chamber is forced out of the sub-chamber and through the fluid lines connected to the carrier. As the pressurized fluid is removed from the sub-chambers (e.g., by vacuum), dialysate is pulled into the sub-chamber. The pumps are typically operated in an alternating fashion such that one pump expels dialysate from its chamber as the other pump pulls dialysate into its chamber and vice versa. This helps to ensure a constant circulation of dialysate though the dialysate circuit formed by the lines secured to the dialysate component carrier. The pumps can alternatively be simultaneously operated.

While the hemodialysis systems described above control the flow of dialysate through the hemodialsyis machine using two pumps, namely a dialyzer inlet pump and a dialyzer outlet pump, other techniques for controlling the flow of the dialysate can be used. In certain implementations, for example, the dialysate component carrier of the hemodialysis system can be equipped with one or more balancing chambers to control the flow of the dialysate through the system. In some implementations, the system includes a dialyzer outlet pump, a balancing chamber positioned along a fluid passage connecting the dialyzer to the dialyzer outlet pump, and a balancing chamber positioned along a fluid passage connecting the sorbent device to the dialyzer. In such implementations, the operation of the dialyzer outlet pump provides the force required to pump dialysate through the system and the balancing chambers control the volume of dialysate that flows through the system at a given time.

While the hemodialysis systems described above are configured to inject sodium chloride solution and/or dilution water into the dialysate circuit in order to adjust or control sodium levels in the dialysate, other sodium management techniques can be used. In certain implementations, the hemodialysis system includes a deionization column containing a strong acid/strong base resin combination that can be used to remove sodium from the fluid circulating through the system. The column can be formed from a replaceable cartridge. Alternatively, the column can be formed from a deionization polisher. The strong acid/strong base resin combinations can remove sodium from the dialysis solution and control pH. Upon detecting excessive sodium levels within the fluid circulating through the system, a three-way valve can be used to divert the dialysate through the strong acid/strong base ion exchange resin mixture in the column to remove sodium in exchange for water. The dialysate is then returned to the dialysate circuit. Advantageously, this method allows sodium levels to be adjusted without the addition of water to the fluid circulating through the system. Thus, additional reservoir volume is not required to compensate for the dilution. However, an exchange program may be used to regenerate the deionization polisher. The control method for either the dilution or the ion exchange systems could be via electronic feedback from the hemodialysis machine, a separate conductivity probe, or a timed sequence.

While some of the above hemodialysis systems include an inflatable pad positioned between the door of the hemodialysis machine in the blood component carrier, other techniques can alternatively or additionally be used to press the blood component carrier against the front face of the hemodialysis machine. In some implementations, for example, the door of the hemodialysis machine includes mechanical features (e.g., projections, springs, etc.) that mate with blood components and/or blood lines of the blood component carrier to press those blood components and/or blood lines against the front face of the hemodialysis machine.

While the level detector 162 has been described as an ultrasonic device, any of various other types of devices capable of measuring the level of liquid in the air release device can be used.

While the drug pump 164 has been described as being a peristaltic pump, any of various other types of pumps capable of injecting drugs into the bloodstream can be used. In some implementations, for example, the drug pump is a syringe pump adapted to receive a syringe into axially move a plunger of the syringe to inject drugs into the bloodstream. In such implementations, the syringe pump can include a stepper motor in order to drive the plunger.

While certain methods above describe manually shaking or stirring the water and dialysate concentrate mixture, any of various other suitable mixing techniques can be used. In some implementations, the fill/drain container 228 includes a powered mechanism to mix the water and dialysate concentrate.

While the dialysate concentrate has been described as being in powder form, liquid concentrates can alternatively or additionally be used. Similarly, while the dialysate has been described as being made by mixing tap water and concentrate, a pre-packaged container of dialysate can alternatively or additionally be used.

In certain implementations, the systems described above are adapted to connect to the Internet. In such cases, the microprocessor can retrieve patient information and other data from the Internet and use that information and data to achieve desired treatment parameters. The various pumps can, for example, be controlled to deliver desired amounts of fluid at desired rates, according to the particular patient being treated.

While the systems described above have been described as hemodialysis systems, similar arrangements can be used for other types of medical treatments, such as peritoneal dialysis. To use systems similar to those above for peritoneal dialysis, instead of pumping blood through a blood circuit, dialysate would be pumped through a second dialysate circuit. The second dialysate circuit would be connected to a patient's abdomen and the other dialysate circuit would remains substantially similar to those dialysate circuits described above. Dialysate could be introduced into the patient's abdomen and then removed and circulated through the second dialysate circuit. Toxins from the dialysate exiting the patient would be removed within the dialyzer and transferred to the dialysate circulating through the other dialysate circuit. The cleansed dialysate (i.e., the dialysate from which the toxins were removed) could then be sent back to the patient.

Other implementations are within the scope of the following claims.

What is claimed is:

1. A dialysis system, comprising:
    a first dialysate pump disposed above a cavity of a housing;
    a slidable drawer defining a recess configured to receive the first dialysate pump, the drawer being at least partially disposed within the cavity in a manner such that when the drawer is moved to a closed position within the cavity, a member of the drawer is lifted towards the first dialysate pump positioned above the cavity;
    a dialysate line secured to a dialysate component carrier that is configured to be supported by the member of the drawer, the dialysate line extending across an aperture that is defined by the dialysate component carrier and that is configured to receive the first dialysate pump, such that when the drawer is moved to the closed position and the member of the drawer is lifted towards the first dialysate pump, the first dialysate pump is received in the aperture and deflects the dialysate line into the recess of the slidable drawer such that the first dialysate pump can pump dialysate through the dialysate line;
    a sorbent device;
    a dialysate reservoir fluidly connected to the sorbent device and arranged to collect dialysate exiting the sorbent device; and
    a second dialysate pump in fluid communication with the sorbent device, positioned upstream of the sorbent device, and configured to introduce dialysate into the sorbent device;
    wherein the first dialysate pump is in fluid communication with the dialysate reservoir, is positioned downstream of the sorbent device, and is configured to draw dialysate out of the dialysate reservoir.

2. The dialysis system of claim 1, wherein the sorbent device is absorbent.

3. The dialysis system of claim 1, wherein the dialysate reservoir is vented to atmosphere.

4. The dialysis system of claim 1, wherein the first dialysate pump is adapted to draw fluid from the dialysate reservoir at substantially the same rate that the second dialysate pump introduces dialysate into the sorbent device.

5. The dialysis system of claim 1, further comprising a connector line that fluidly connects the sorbent device to the dialysate reservoir.

6. The dialysis system of claim 5, wherein one end of the connector line is connected to a top region of the sorbent device, and another end of the connector line is connected to a top region of the dialysate reservoir.

7. The dialysis system of claim 1, wherein the sorbent device and the dialysate reservoir sit on a weight scale.

8. The dialysis system of claim 7, further comprising a microprocessor connected to the scale and the first and second dialysate pumps.

9. The dialysis system of claim 8, wherein the microprocessor is adapted to control the first and second dialysate pumps in a manner so as to maintain a substantially constant weight on the scale.

* * * * *